(12) United States Patent
Hara et al.

(10) Patent No.: US 11,642,019 B2
(45) Date of Patent: May 9, 2023

(54) OPHTHALMIC DEVICE

(71) Applicant: Tomey Corporation, Nagoya (JP)

(72) Inventors: Naoko Hara, Nagoya (JP); Chihiro Kato, Nagoya (JP); Keiichiro Okamoto, Nagoya (JP)

(73) Assignee: Tomey Corporation, Nagoya (JP)

( * ) Notice: Subject to any disclaimer, the term of this patent is extended or adjusted under 35 U.S.C. 154(b) by 286 days.

(21) Appl. No.: 16/999,937

(22) Filed: Aug. 21, 2020

(65) Prior Publication Data

US 2021/0059519 A1     Mar. 4, 2021

(30) Foreign Application Priority Data

Aug. 30, 2019 (JP) .............................. JP2019-157609

(51) Int. Cl.
*A61B 3/10*    (2006.01)
*A61B 3/14*    (2006.01)
*A61B 3/00*    (2006.01)

(52) U.S. Cl.
CPC ............ *A61B 3/102* (2013.01); *A61B 3/0008* (2013.01); *A61B 3/0041* (2013.01); *A61B 3/14* (2013.01)

(58) Field of Classification Search
CPC ..... A61B 3/102; A61B 3/0008; A61B 3/0041; A61B 3/14; A61B 3/0025; A61B 3/0058
USPC ........................................................ 351/206
See application file for complete search history.

(56) References Cited

U.S. PATENT DOCUMENTS

| 5,836,872 A | 11/1998 | Kenet et al. |
| 2006/0002678 A1 | 1/2006 | Weber et al. |
| 2006/0187462 A1* | 8/2006 | Srinivasan ........... A61B 5/0066 356/479 |
| 2009/0254302 A1* | 10/2009 | Jennings ................. G01S 7/412 702/155 |
| 2012/0189184 A1 | 7/2012 | Matsumoto et al. |

(Continued)

FOREIGN PATENT DOCUMENTS

| JP | 2011-025046 A | 2/2011 |
| JP | 2011-087651 A | 5/2011 |

(Continued)

OTHER PUBLICATIONS

The extended European search report issued by the European Patent Office dated May 3, 2021, which corresponds to European Application No. 20191274.8-1126 and is related to U.S. Appl. No. 16/999,937.

(Continued)

*Primary Examiner* — Mohammed A Hasan
(74) *Attorney, Agent, or Firm* — Studebaker & Brackett PC

(57) ABSTRACT

An ophthalmic device includes a two-dimensional image acquisition unit that acquires a two-dimensional image by photographing the front of an eye to be examined with a color camera; a three-dimensional image acquisition unit that acquires a three-dimensional image of the eye to be examined by optical coherence tomography; and a correspondence definition data generation unit that generates correspondence definition data in which the position of a predetermined site of the eye to be examined in the three-dimensional image when the predetermined site is photographed as the three-dimensional image is associated with the position of the predetermined site in the two-dimensional image when the predetermined site is photographed as the two-dimensional image.

20 Claims, 7 Drawing Sheets

(56) References Cited

U.S. PATENT DOCUMENTS

| | | | |
|---|---|---|---|
| 2013/0194544 A1 | 8/2013 | Iwase et al. | |
| 2014/0313480 A1* | 10/2014 | Ohta | A61B 3/0025 |
| | | | 351/246 |
| 2017/0027437 A1* | 2/2017 | Neal | A61B 3/1005 |
| 2017/0273558 A1 | 9/2017 | Tamura | |

FOREIGN PATENT DOCUMENTS

| | | | |
|---|---|---|---|
| JP | 2011-177273 A | 9/2011 | |
| JP | 2012-081330 A | 4/2012 | |
| JP | 2016-054854 A | 4/2016 | |
| JP | 2017-000469 A | 1/2017 | |
| JP | 2019-042304 A | 3/2019 | |

OTHER PUBLICATIONS

An Office Action; "Notification of Reasons for Refusal," mailed by the Japanese Patent Office dated Mar. 29, 2023, which corresponds to Japanese Patent Application No. 2019-157609 and is related to U.S. Appl. No. 16/999,937, with English language translation.

* cited by examiner

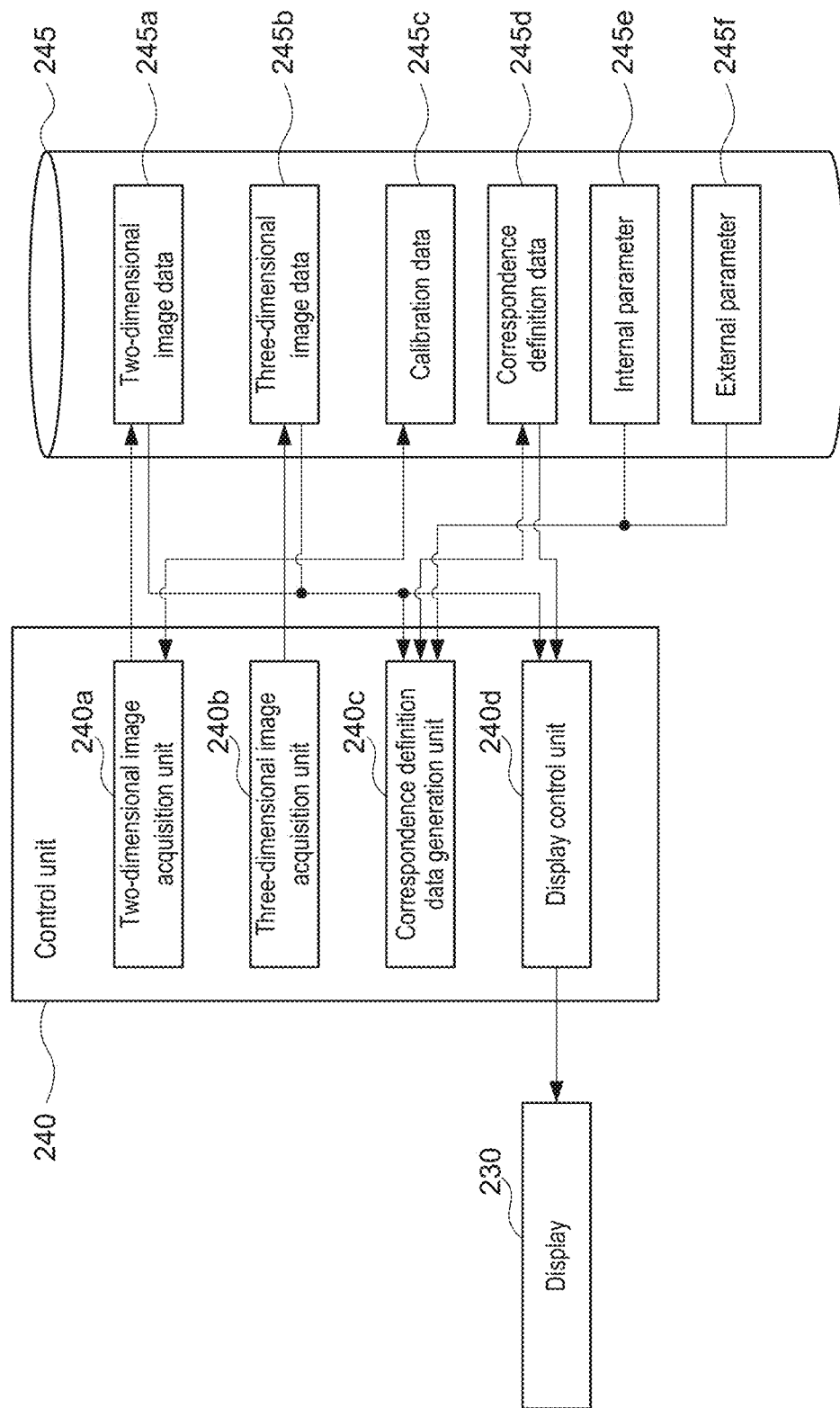

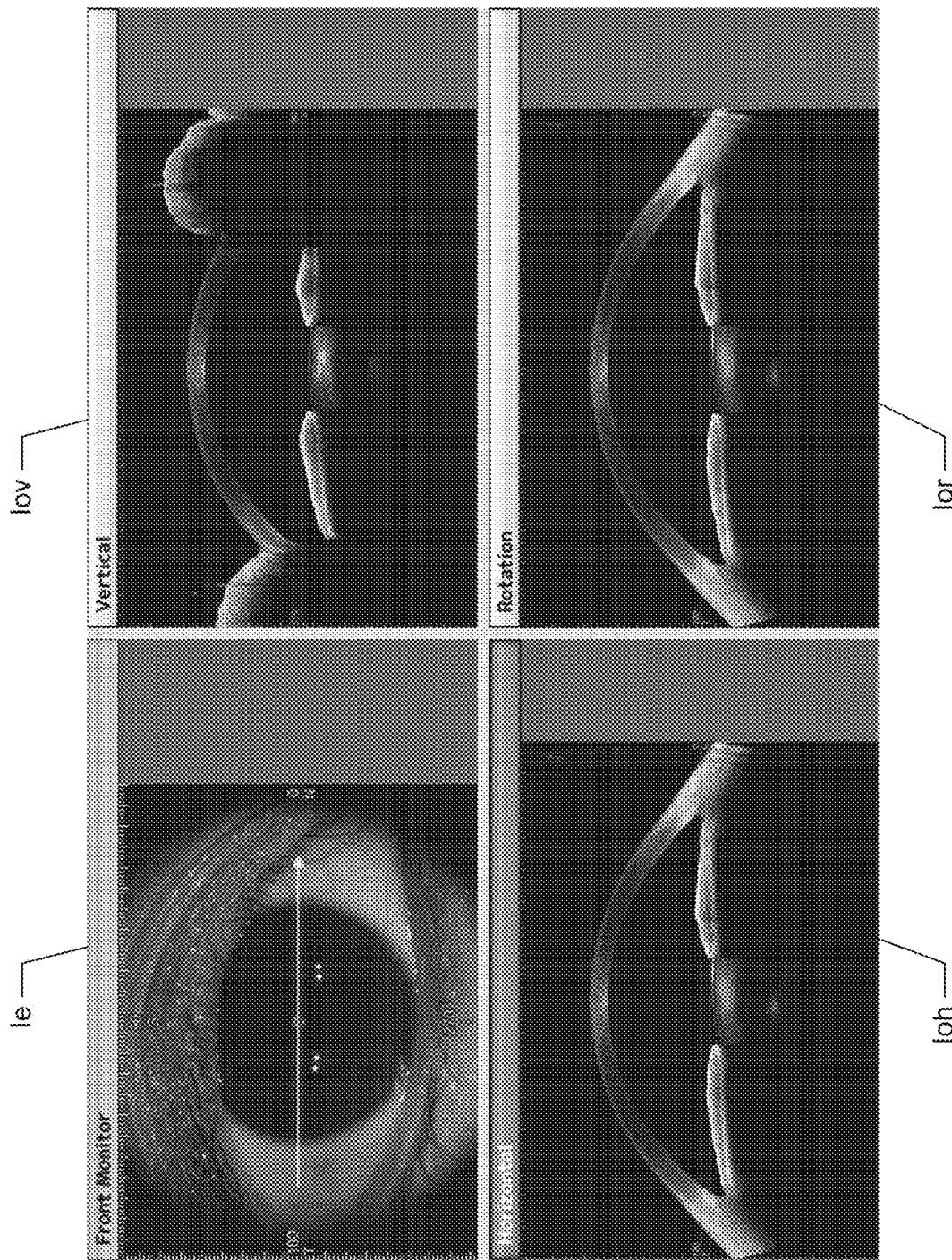

OPHTHALMIC DEVICE

CROSS-REFERENCE TO RELATED APPLICATION

This application claims benefit of priority to Japanese Patent Application No. 2019-157609, filed Aug. 30, 2019, the entire content of which is incorporated herein by reference.

BACKGROUND

Technical Field

The present disclosure relates to an ophthalmic device.

Background Art

Conventionally, optical coherence tomography (OCT) that acquires a three-dimensional image based on a tomographic image of an eye to be examined is known. Various methods are known as methods for acquiring a three-dimensional image of the eye to be examined by optical coherence tomography, as described, for example, in JP 2017-469 A. Further, JP 2019-42304 A discloses a configuration in which light is projected/received along an optical axis inclined with respect to the eye axis of the eye to be examined to capture an entire periphery image of the iridocorneal angle, cross-sectional information of the iridocorneal angle is acquired by optical coherence tomography, and the entire periphery image is associated with the cross-sectional information in regard to the positional relationship.

SUMMARY

When inspection and diagnosis are performed using a three-dimensional image obtained by optical coherence tomography as in JP 2017-469 A, a two-dimensional image is often used together. For example, by displaying a two-dimensional color image together with a three-dimensional image, inspection and diagnosis can be performed based on the colors of the eye to be examined. However, in the conventional configuration, it is difficult to associate the three-dimensional image with the two-dimensional image. For example, when it is desired to specify the color of a specific site shown in a three-dimensional image, it is conventionally necessary to compare a two-dimensional image captured with a color camera with a three-dimensional image expressed in gray scale. However, even when a site to be focused on is found in the three-dimensional image, it is sometimes difficult to associate this site in the three-dimensional image with the corresponding site in the two-dimensional image. In this case, it is difficult to specify the color of the site to be focused on. In addition, there is a case where it is desired to specify, in the three-dimensional image, the structure of a specific color site shown in the two-dimensional image. In this case, even when a site to be focused on is found in the two-dimensional image, it is sometimes difficult to associate this site in the two-dimensional image with the corresponding site in the three-dimensional image. In this case, it is difficult to specify the three-dimensional structure corresponding to the focused color site.

Further, in JP 2019-42304 A, the entire periphery image of the iridocorneal angle and the cross-sectional information thereof are associated in regard to the positional relationship, but this document does not disclose association between the cross-sectional information and any other image for an arbitrary site of the eye to be examined, for example, iris or blood vessels on the surface of the eye to be examined. Therefore, it is not possible to specify the color of the site visually recognized when the eye to be examined is viewed from the front on the three-dimensional image. Accordingly, the present disclosure discloses embodiments to associate a local structure of an eye to be examined with a color developing in the front of the eye to be examined.

An ophthalmic device includes a two-dimensional image acquisition unit that acquires a two-dimensional image by photographing the front of an eye to be examined with a color camera; a three-dimensional image acquisition unit that acquires a three-dimensional image of the eye to be examined by optical coherence tomography; and a correspondence definition data generation unit that generates correspondence definition data in which the position of a predetermined site of the eye to be examined in the three-dimensional image when the predetermined site is photographed as the three-dimensional image is associated with the position of the predetermined site in the two-dimensional image when the predetermined site is photographed as the two-dimensional image. Further, instead of, or in addition to, the correspondence definition data generation unit, a display control unit that displays a three-dimensional image colored with the colors shown in the two-dimensional image on a display unit can be adopted.

That is, when the correspondence definition data in which the position of the specific site in the three-dimensional image is associated with the position thereof in the two-dimensional image is obtained, the correspondence definition data can be used to associate the three-dimensional structure of the eye to be examined with the colors photographed as the two-dimensional image. As a result, a local structure of the eye to be examined and its color can be associated with each other. Furthermore, if a local position in the three-dimensional image is colored with a color of the two-dimensional image and displayed, the examiner can easily associate the local structure of the eye to be examined with the color developing in the front of the eye to be examined.

BRIEF DESCRIPTION OF THE DRAWINGS

FIG. 3 is a diagram showing a configuration related to arithmetic process;

FIG. 4 is a diagram showing a display example of a two-dimensional image and three-dimensional images;

DETAILED DESCRIPTION

Embodiments of the present disclosure will be described in the following order.

(1) Configuration of ophthalmic device:
(2) Configuration of control unit:
(3) Calibration data generation process:

(4) Photographing process:
(4-1) Correspondence definition data generation process:
(5) Other Embodiments:

(1) Configuration of Ophthalmic Device

Figure 1:
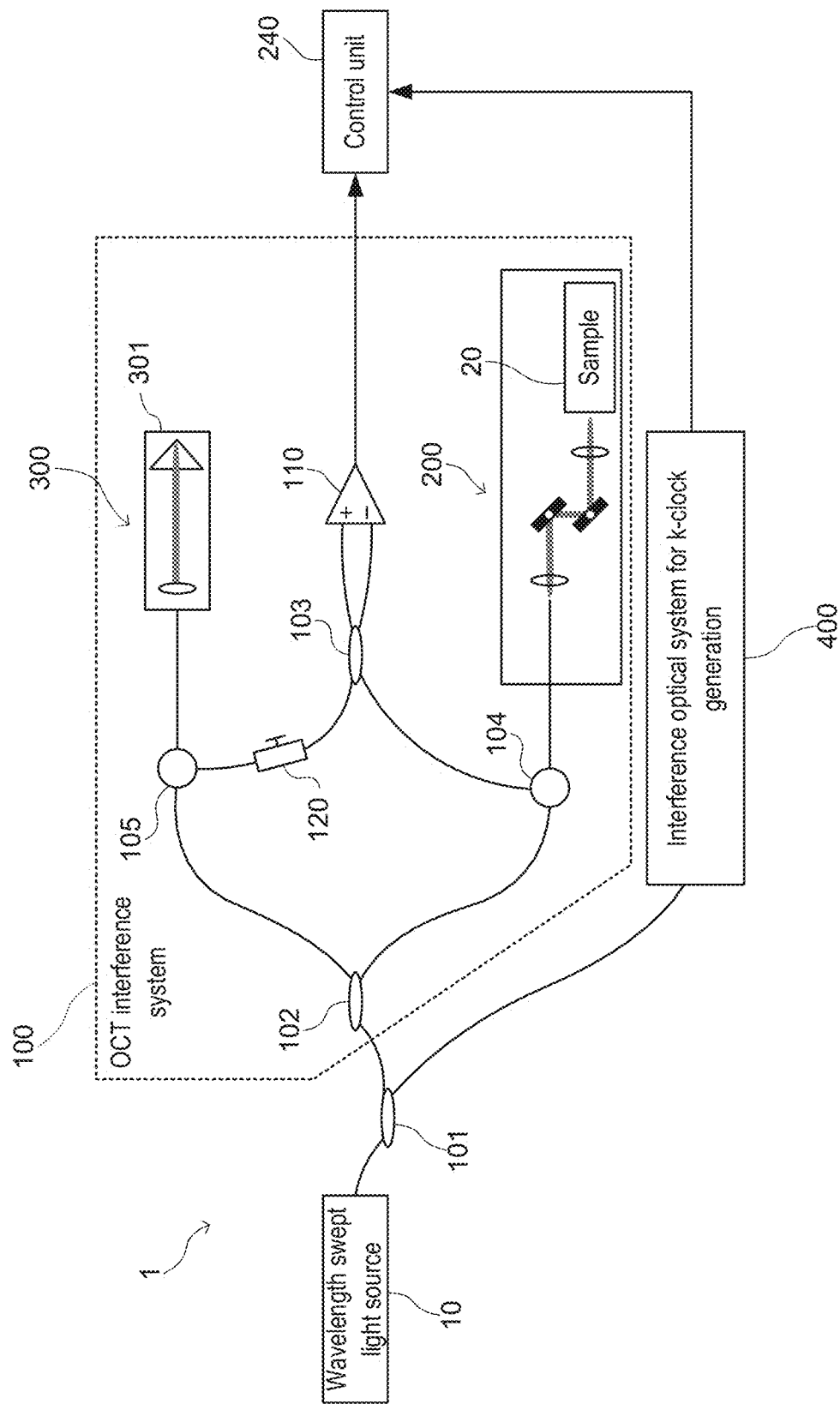
FIG. 1 is a diagram showing a configuration of an optical coherence tomographic device 1 according to an embodiment of the present disclosure.

An optical coherence tomographic device 1 which is an ophthalmic device according to an example of the present disclosure will be described below. FIG. 1 is a diagram showing a configuration of the optical coherence tomographic device 1 according to an embodiment of the present disclosure. The optical coherence tomographic device 1 roughly includes an OCT interference system 100, a k-clock generating interference optical system 400, and a control unit 240.

The OCT interference system 100 is an optical system for obtaining a tomographic image of the anterior segment of an eye to be examined by optical coherence tomography. In the present example, SS-OCT (Swept Source-OCT) is adopted, and a wavelength swept light source 10 is a light source that outputs light while varying and scanning the wavelength with time. The wavelength swept light source 10 is, for example, a light source which has a band with a central wavelength of 1 μm or more and a sweep width of 70 nm or more and also which has performance capable of realizing high-speed scanning of 50 KHz or more. The input light emitted from the wavelength swept light source 10 is guided by an optical fiber such as a single mode fiber, and used for tomographic image capturing of a sample 20 and also for k-clock generation.

An SMFC (single mode fiber coupler) 101 for branching the emitted input light is provided between the wavelength swept light source 10, and the OCT interference system 100 and the k-clock generating interference optical system 400, respectively. The input light is branched by the SMFC 101 into lights toward the OCT interference system 100 and the k-clock generating interference optical system 400.

The OCT interference system 100 includes SMFCs 102 and 103, a measurement-side circulator 104, a reference-side circulator 105, a balanced detector 110, a polarization controller 120, a scanning-alignment optical system 200, and a reference optical system 300. The SMFC 102 is a device on which the one light into which the input light is branched by the SMFC 101 is incident. It branches the incident input light, and guides the one light toward the scanning-alignment optical system 200 and the other light toward the reference optical system 300.

That is, the one light into which the incident input light is branched by the SMFC 102 is input to the scanning-alignment optical system 200 via the measurement-side circulator 104, and becomes measurement light for measuring the sample 20. The other light into which the incident input light is branched by the SMFC 102 is input to the reference optical system 300 via the reference-side circulator 105 and becomes reference light.

The light incident on the sample 20 is reflected by the sample, and is input, as the measurement light, to the SMFC 103 via the measurement-side circulator 104. The light incident on the reference optical system 300 becomes the reference light by the reference unit 301, is output from the reference optical system 300, and is input to the SMFC 103 via the reference-side circulator 105 and the polarization controller 120.

The measurement light and the reference light, when being input to the SMFC 103, are combined by the SMFC 103 to generate measurement interference light. The measurement interference light is input to the balanced detector 110. The balanced detector 110 receives the measurement interference light, and outputs a measurement interference signal. The measurement interference signal is input to the control unit 240 that obtains the tomographic image of the sample 20 based on the measurement interference signal.

The scanning-alignment optical system 200 is an optical system for irradiating the sample 20 with the light input from the measurement-side circulator 104 and guiding the light reflected from the sample 20 to the SMFC 103. Details of the scanning-alignment optical system 200 will be described later.

The measurement-side circulator 104 is an optical element arranged between the scanning-alignment optical system 200, and the SMFC 102 and the SMFC 103, respectively. By the measurement-side circulator 104, the measurement light guided from the SMFC 102 is guided to the scanning-alignment optical system 200, and the reflected light guided from the scanning-alignment optical system 200 is guided to the SMFC 103.

The reference optical system 300 is provided with a reference unit 301 that converts the input light into the reference light, and a reference-side circulator 105 that guides the input light to the reference optical system 300 and guides the reference light to the SMFC 103. In the present example, the reference unit 301 is a prism that emits the incident input light as the reference light. The reference unit 301 is configured to be movable to match the optical path length of the scanning-alignment optical system 200 with the optical path length of the reference optical system 300 before the measurement of the sample 20. The position of the reference unit 301 is fixed during the measurement of the sample 20.

The reference-side circulator 105 is an optical element arranged between the reference unit 301, and the SMFC 102 and the SMFC 103, respectively. The input light guided from the SMFC 102 is guided to the reference unit 301 by the reference-side circulator 105, and the reference light guided from the reference unit 301 is guided to the SMFC 103 by the reference-side circulator 105. The SMFC 103 combines the reflected light guided from the scanning-alignment optical system 200 and the reference light guided from the reference optical system 300 to generate measurement interference light. Further, the SMFC 103 branches the combined measurement interference light into two measurement interference lights which are different in 180° phase, and guides them to the balanced detector 110.

The balanced detector 110 is a photodetector that receives the measurement interference light combined by the SMFC 103. The SMFC 103 is arranged between the scanning-alignment optical system 200 and the reference optical system 300, and the balanced detector 110, and the polarization controller 120 is arranged between the reference optical system 300 and the SMFC 103.

The polarization controller 120 is an element that controls the polarization of the reference light guided from the reference optical system 300 to the SMFC 103. As the polarization controller 120, various modes of controllers such as an in-line type and a paddle type can be used without any particular limitation. The control unit 240 is a device that obtains a tomographic image of the sample 20 based on the measurement interference signal output from the balanced detector 110, and the tomographic image obtained here is displayed on a display 230.

Figure 2:
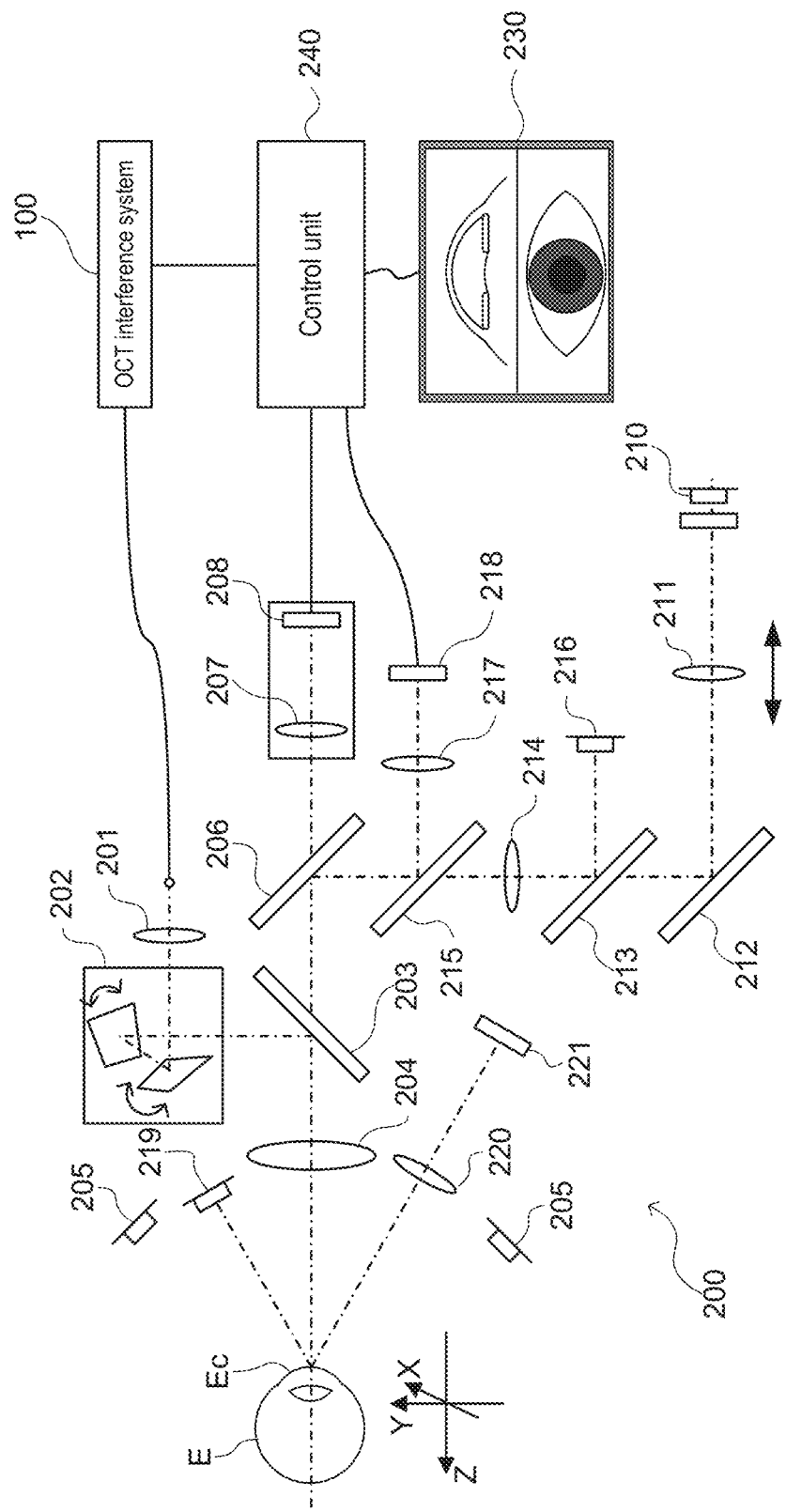
FIG. 2 is a schematic diagram illustrating a configuration of a scanning-alignment optical system.

FIG. 2 shows a configuration of the scanning-alignment optical system 200. The scanning-alignment optical system 200 includes a scanning optical system, an anterior segment photographing system, a fixation target optical system, and an alignment optical system. In the scanning optical system, the light output from the SMFC 102 is input to the measurement-side circulator 104 and further input from the measurement-side circulator 104 to a galvanometer scanner 202 through a collimator lens 201.

The galvanometer scanner 202 is a device for scanning the input light, and is driven by a galvanometer driver (not shown). The input light output from the galvanometer scanner 202 is reflected at an angle of 90° by a hot mirror 203, and is incident on an eye E to be examined through an objective lens 204. The input light incident on the eye E to be examined is reflected at tissue portions (cornea, anterior chamber, iris, crystalline lens, etc.) of an anterior segment Ec, and becomes measurement light. The measurement light passes through the objective lens 204, the hot mirror 203, the galvanometer scanner 202, and the collimator lens 201 in this order, contrary to the above, and is input to the SMFC 103 via the measurement-side circulator 104.

Then, in the SMFC 103, the reflected light from the anterior segment Ec and the reference light are combined to generate a signal, and the signal is input to the balanced detector 110. In the balanced detector 110, the interference at each wavelength is measured, and the measurement interference signal measured is input to the control unit 240. The control unit 240 performs processes such as inverse Fourier transform on the measurement interference signal, so that a tomographic image of the anterior segment Ec along the scanning line is acquired.

The anterior segment photographing system includes white light sources 205, 205, the objective lens 204, the hot mirror 203, a beam splitter 206, an imaging lens 207, and an area sensor 208. The white light sources 205, 205 are configured to irradiate the front of the eye E to be examined with illumination light in a visible light region, and the reflected light from the eye E to be examined passes through the objective lens 204, the hot mirror 203, the beam splitter 206, and the imaging lens 207, and is input to the area sensor 208. As a result, a front image of the eye E to be examined is captured, and the captured two-dimensional image is processed by the control unit 240.

In the present embodiment, the white light sources 205 are light sources that output white light. The white light has only to have a spectral distribution such that the eye E to be examined irradiated with the white light can be visually recognized in full color. In order to accurately reproduce the colors of the eye E to be examined, the white light sources 205 are preferably light sources having a high color rendering property, and, for example, preferably have an average color rendering index (Ra) of 80 or more. In the present embodiment, the average color rendering index (Ra) of the white light sources 205 is 95.

Further, in the present embodiment, explanation is given on the premise that the white light sources 205 have a color temperature of 5500 K, but the color temperature is not limited. In the present embodiment, the image data output from the area sensor 208 is data in which gradation values are designated for each pixel arranged two-dimensionally, the gradation values each indicating the detection intensity of light of each color of RGB (R: red, G: green, and B: blue). In the present embodiment, the anterior segment photographing system corresponds to a color camera.

The fixation target optical system is an optical system for causing the subject to gaze at the fixation lamp in order to prevent the subject from moving his/her eyeball (eye E to be examined) as much as possible. In the present embodiment, the fixation target optical system is composed of a fixation target light source 210, a varifocal movable lens 211, a cold mirror 212, a hot mirror 213, a relay lens 214, a beam splitter 215, the beam splitter 206, the hot mirror 203, and the objective lens 204. As a result, the light output from the fixation target light source 210 is configured to be output to the eye E to be examined via the varifocal movable lens 211, the cold mirror 212, the hot mirror 213, the relay lens 214, the beam splitter 215, the beam splitter 206, the hot mirror 203, and the objective lens 204 in this order.

Here, the varifocal movable lens 211 is configured to be movable so that the focus of the fixation target can be freely changed. Specifically, the varifocal movable lens 211 is moved to an arbitrary position, so that the focus of the fixation target comes, for example, to the position of the refractive power value of the eye E to be examined By doing so, it becomes possible to establish a state in which the subject can see the fixation target naturally (a state in which no load is applied to the crystalline lens) for performing measurement. Also, when it is used, for example, for research on the focus adjustment function of the crystalline lens, it becomes possible to photograph the state of natural vision and the state in which adjustment load is applied to the crystalline lens by moving the varifocal movable lens 211 so that the focus of the fixation target can be seen closer than in natural vision to compare the shapes of the crystalline lens, or to gradually move the varifocal movable lens 211 to capture a moving image of the change in shape of the crystalline lens.

The alignment optical system is composed of an XY-direction position detection system for detecting the position of the eye E to be examined (corneal apex) in the XY direction (vertical and horizontal displacement relative to the main body) and a Z-direction position detection system for detecting the position of the eye E to be examined (corneal apex) in the longitudinal direction (Z direction). The XY-direction position detection system includes an XY-position detection light source 216, the hot mirror 213, the relay lens 214, the beam splitter 215, the beam splitter 206, the hot mirror 203, the objective lens 204, an imaging lens 217, and a two-dimensional position sensor 218. From the XY-position detection light source 216, alignment light for position detection is output, and emitted toward the anterior segment Ec (cornea) of the eye E to be examined via the hot mirror 213, the relay lens 214, the beam splitter 215, the beam splitter 206, the hot mirror 203, and the objective lens 204.

At this time, the corneal surface of the eye E to be examined has a spherical shape, and thus the alignment light is reflected on the corneal surface so as to form a bright spot image inside the corneal apex of the eye E to be examined, and the reflected light is incident from the objective lens 204. The reflected light (bright spot) from the corneal apex is input to the two-dimensional position sensor 218 via the objective lens 204, the hot mirror 203, the beam splitter 206, the beam splitter 215, and the imaging lens 217. By detecting the position of the bright spot by the two-dimensional position sensor 218, the position of the corneal apex (the position in each of the X and Y directions) is detected.

The detection signal of the two-dimensional position sensor 218 is input to the control unit 240. In the present embodiment, a predetermined (normal) image acquisition position of the corneal apex (position which should be followed during tomographic image acquisition), in the case where the two-dimensional position sensor 218 and the anterior segment photographing system are aligned, is pre-set. The normal image acquisition position of the corneal apex is, for example, the center position of a captured image of an imaging element or the like. Based on the detection by the two-dimensional position sensor 218, the control unit 240 obtains the amount of positional deviation between the normal position and the detected position of the corneal apex (bright spot) in each of the X and Y directions.

The Z-direction position detection system includes a Z-position detection light source 219, an imaging lens 220, and a line sensor 221. The Z-position detection light source 219 is configured to irradiate the eye E to be examined with detection light (slit light or spot light) from an oblique direction so that the obliquely reflected light from the cornea is incident on the line sensor 221 through the imaging lens 220. At this time, the incident position of the reflected light incident on the line sensor 221 differs depending on the position of the eye E to be examined in the longitudinal direction (Z direction), and thus the position of the eye E to be examined in the Z direction is detected.

Here, although not shown, the device main body of the optical coherence tomographic device 1 is supported so as to be movable in the X direction (horizontal direction) and the Y direction (vertical direction) as well as the Z direction (longitudinal direction) with respect to a holding table. The control unit 240 causes the device main body to freely move in the X direction, the Y direction, and the Z direction with respect to the holding table. In addition, a chin rest on which the subject puts his/her chin and a forehead pad on which the subject puts his/her forehead are fixedly provided on the front side (subject side) of the device main body, and the subject's eye (eye E to be examined) is arranged in front of an inspection window provided in the front surface of the device main body. The control unit 240 causes the device main body to move with respect to the holding table so that the amounts of positional deviation, in the X and Y directions, of the corneal apex (bright spot) detected by the XY-direction position detection system and the amount of positional deviation of the eye E to be examined detected by the Z-direction position detection system are all zero.

The k-clock generating interference optical system 400 shown in FIG. 1 is a device that optically generates a sample clock (k-clock) from the input light branched from the SMFC 101 in order to sample the measurement interference signal at equal-interval frequencies. Then, the generated k-clock signal is output to the control unit 240. As a result, distortion of the measurement interference signal is suppressed, and deterioration of resolution is prevented.

(2) Configuration of Control Unit

In the present embodiment, the control unit 240 includes a CPU, a RAM, a ROM, and the like (not shown). The control unit 240 can execute a program stored in a storage medium 245 and execute various arithmetic processes using the data stored in the storage medium 245 included in the optical coherence tomographic device 1. The control unit 240 can control control targets included in the OCT interference system 100, the scanning-alignment optical system 200, the reference optical system 300, and the k-clock generating interference optical system 400, for example, a motor for alignment, an area sensor 208, and the like.

Further, the control unit 240 can execute arithmetic process based on the information output from the OCT interference system 100, the scanning-alignment optical system 200, and the like. In the present embodiment, the control unit 240 performs processes on the basis of the three-dimensional image output from the OCT interference system 100 and the two-dimensional image output from the scanning-alignment optical system 200 so that the positions in both the images can be associated with each other.

FIG. 3 is a diagram showing a configuration related to arithmetic process for associating the positions. The control unit 240 functions as a two-dimensional image acquisition unit 240a, a three-dimensional image acquisition unit 240b, a correspondence definition data generation unit 240c, and a display control unit 240d upon execution of programs (not shown). The two-dimensional image acquisition unit 240a is a program module that causes the control unit 240 to perform a function of acquiring a two-dimensional image of the eye E to be examined with the color camera.

That is, the control unit 240 can control the anterior segment photographing system (area sensor 208 or the like) that functions as the color camera to acquire a two-dimensional image of the subject existing in the visual field of the color camera, using the function of the two-dimensional image acquisition unit 240a. Therefore, when a two-dimensional image is acquired in the state in which the subject puts his/her chin on the chin rest of the optical coherence tomographic device 1 and puts his/her forehead on the forehead pad thereof so that the subject's eye (eye E to be examined) is arranged in front of the inspection window provided in the front surface of the device main body, a two-dimensional image of the eye E to be examined is acquired. When photographing arbitrary objects put in the portion where the eye E to be examined is to be arranged, such as a color chart, a target for white balance adjustment and a calibration structure (all of which will be described later), it is possible to acquire two-dimensional images of these objects.

In any case, when the two-dimensional image is acquired, two-dimensional image data 245a indicating the two-dimensional image is recorded in the storage medium 245. In the present embodiment, the two-dimensional image data is data in which gradation values are designated for each pixel arranged two-dimensionally, the gradation values each indicating the detection intensity of light of each channel of RGB (R: red, G: green, and B: blue). In the present embodiment, the coordinates representing the position of each pixel of the two-dimensional image are represented as (u, v). u is a variable indicating the position in the horizontal direction (direction parallel to the X direction), and v is a variable indicating the position in the vertical direction (direction parallel to the Y direction).

Note that in the present embodiment, the gradation value indicated by the two-dimensional image data 245a can take a value of 0 to 255 for each of RGB. In the present embodiment, when a specific color is captured and the two-dimensional image data 245a is obtained, the color output onto a display or a printer by the two-dimensional image data 245a often does not match the captured specific color. In this sense, the gradation values of the two-dimensional image data 245a (the gradation values before correction by calibration data 245c which will be described later) indicate the colors expressed in a device-dependent color space.

In the present embodiment, the control unit 240 displays the captured two-dimensional image on the display 230, using the function of the display control unit 240d. That is, when the two-dimensional image data 245a is acquired, the control unit 240 controls the display 230 so that the two-dimensional image indicated by the two-dimensional image data 245a is displayed at a predetermined position. FIG. 4 is a diagram showing a display example of a two-dimensional image Ie. Although not shown in FIG. 4, the two-dimensional image Ie is a color image.

Further, in the present embodiment, the two-dimensional image Ie to be displayed on the display 230 is an image in a state in which colors are configured by the calibration data 245c which will be described later. In the present embodiment, the calibration data 245c is data for converting gradation values in the two-dimensional image into gradation values in a reference color space, and is also data indicating a conversion formula for converting the colors of the subject indicated by the gradation values in the two-dimensional image into gradation values when the colors are expressed in the reference color space which is a device-independent color space. The control unit 240 corrects the two-dimensional image data 245a on the basis of the calibration data 245c, and provides data in which the colors are expressed using the reference color space. The control unit 240 updates the two-dimensional image data 245a with the corrected data. In the display 230, color matching in which the colors expressed using the reference color space are expressed in the designated colors has already been performed. So, the colors displayed on the display 230 are equivalent to the colors of the eye E to be examined visually recognized by the examiner.

The three-dimensional image acquisition unit 240b is a program module that causes the control unit 240 to perform a function of acquiring a three-dimensional image of the eye E to be examined by optical coherence tomography. That is, the control unit 240 controls the OCT interference system 100, the scanning-alignment optical system 200 (such as the galvanometer scanner 202), and the k-clock generating interference optical system 400 to acquire the measurement interference signal, using the function of the three-dimensional image acquisition unit 240b. The control unit 240 performs processes such as inverse Fourier transform on the measurement interference signal to acquire a tomographic image of the anterior segment Ec along the scanning line.

The control unit 240 changes the scanning direction of the galvanometer scanner 202, and acquires tomographic images for a plurality of sections. In the present embodiment, a three-dimensional image of the eye E to be examined is acquired by acquiring tomographic images of the plurality of sections covering the entire anterior segment of the eye E to be examined. The scanning direction of the galvanometer scanner 202 may be various. For example, the entire anterior segment of the eye E to be examined may be covered by setting a plurality of sections, which are parallel to the X and Z directions, at regular intervals in the Y direction. In addition, assuming a section that passes through the corneal apex and is parallel to the Z direction, the entire anterior segment of the eye E to be examined may be covered by rotating the section at a constant angle with an axis that passes through the corneal apex and is parallel to the Z direction as the rotation axis.

Each of the plurality of tomographic images shows lightness and darkness according to the structure of the eye E to be examined for each position of the section. Therefore, the control unit 240 sets each position of the plurality of tomographic images as three-dimensional image data 245b having one-channel information indicating lightness and darkness for each coordinate in the coordinate system in the optical coherence tomography, and records the data in the storage medium 245. It should be noted that the coordinates indicated by the three-dimensional image data 245b have only to be expressed in a predefined coordinate system, and an example in which the three-dimensional image data 245b is defined in the XYZ coordinate system used for alignment is assumed in the present embodiment. That is, the three-dimensional image data 245b is data in which gradation values are designated, according to the structure of the eye E to be examined, for a plurality of coordinates in the XYZ coordinate system. In the present embodiment, the coordinates in the XYZ coordinate system are represented as (X, Y, Z).

In the present embodiment, the control unit 240 displays the captured three-dimensional image on the display 230, using the function of the display control unit 240d. That is, when the three-dimensional image data 245b is acquired, the control unit 240 controls the display 230 so that the three-dimensional image of an arbitrary portion indicated by the three-dimensional image data 245b is displayed at a predetermined position. FIG. 4 shows an example in which a vertical tomographic image (section parallel to the Y and Z directions) Iov is displayed on the right side of the two-dimensional image Ie. Further, FIG. 4 shows an example in which a horizontal tomographic image (section parallel to the X and Z directions) Ioh is displayed below the two-dimensional image Ie, and a tomographic image Ior of a section rotated by an arbitrary angle with respect to an axis which passes through the corneal apex and is parallel to the Z direction is displayed on the lower right side of the two-dimensional image Ie. These tomographic images Iov, Ioh, and Ior are of the section and thus are two-dimensional, but display part of the three-dimensional image data 245b and thus can also be said to provide three-dimensional image display.

As described above, the three-dimensional image data 245b is data having a gradation value of one channel for each of a plurality of coordinates in the XYZ coordinate system. Therefore, when the tomographic images Iov, Ioh, and Ior are displayed based on the three-dimensional image data 245b, they are usually grayscale images. However, when inspection and diagnosis are performed using three-dimensional images, or when an artificial eye is created using three-dimensional images, it is preferable that the color for each site of the eye E to be examined be a color visually recognized by a person.

Therefore, the present embodiment has a configuration in which each site having a three-dimensional structure obtained by optical coherence tomography is colored based on the two-dimensional image. For the coloring, correspondence definition data in which three-dimensional coordinates of the three-dimensional image are associated with two-dimensional coordinates of the two-dimensional image is generated in the present embodiment. Specifically, the correspondence definition data generating unit 240c is a program module that causes the control unit 240 to perform a function of generating correspondence definition data in which the position of a predetermined site of the eye E to be examined in the three-dimensional image when the predetermined site is photographed as the three-dimensional image is associated with the position of the predetermined site in the two-dimensional image when the predetermined site is photographed as the two-dimensional image. That is, in the present embodiment, the control unit 240 generates the correspondence definition data 245d to associate the three-dimensional coordinates of the three-dimensional image with the two-dimensional coordinates of the two-dimensional image, and the three-dimensional image is colored by using correspondence definition data 245d.

In the present embodiment, the correspondence definition data 245d is data in which the three-dimensional coordinates of the three-dimensional image are associated with the two-dimensional coordinates of the two-dimensional image. That is, in the two-dimensional image, the gradation value is defined for each color channel of RGB for each pixel forming the two-dimensional image, and the position of each pixel is specified by the two-dimensional coordinates (u, v). Therefore, when the two-dimensional coordinates (u, v) indicating each pixel of the two-dimensional image are specified, the colors are specified. Therefore, by associating arbitrary three-dimensional coordinates (X, Y, Z) of the three-dimensional image with two-dimensional coordinates (u, v) when the portion of the three-dimensional coordinates is photographed as a two-dimensional image, the arbitrary three-dimensional coordinates (X, Y, Z) can be regarded as having been colored.

As described above, the correspondence definition data 245d is data in which the three-dimensional coordinates of the three-dimensional image are associated with the two-dimensional coordinates of the two-dimensional image, and, in the present embodiment, is generated based on the two-dimensional image data 245a and three-dimensional image data 245b obtained by photographing the same eye E to be examined Note that distortion or the like in the optical system of the color camera does not change for each eye E to be examined, but the cornea of the eye E to be examined changes for each eye E to be examined (for each subject).

Therefore, in the present embodiment, with respect to the iris photographed through the cornea, the correspondence is defined for each eye E to be examined by ray tracing. On the other hand, for sites other than the iris (sites outside the iris when the eye E to be examined is viewed from the front), the correspondence is defined based on the relationship between the eye E to be examined and the color camera and the characteristics of the optical system of the color camera. The details of the definition of such correspondence will be described later. In any case, using the function of the correspondence definition data generation unit 240c, the control unit 240 generates the correspondence definition data 245d indicating the correspondence between the three-dimensional coordinates of the three-dimensional image and the two-dimensional coordinates of the two-dimensional image, and records the correspondence definition data 245d, in association with the two-dimensional image data 245a and the three-dimensional image data 245b, in the storage medium 245.

When the correspondence definition data 245d is generated, the correspondence definition data 245d can be used for various purposes. For example, if the two-dimensional image data 245a and the three-dimensional image data 245b, and the correspondence definition data 245d are used as a set in any other output device (for example, a printer), a three-dimensional image of the eye E to be examined colored with colors very close to the actual colors of the eye E to be examined can be output.

In the present embodiment, when the three-dimensional image is displayed on the display 230, the correspondence definition data 245d is used to color each part of the eye E to be examined. That is, the control unit 240 extracts the three-dimensional coordinates existing on an arbitrary section from the three-dimensional image data 245b, using the function of the display control unit 240d. The control unit 240 also refers to the correspondence definition data 245d to specify the two-dimensional coordinates corresponding to the three-dimensional coordinates. Further, the control unit 240 refers to the two-dimensional image data 245a and regards the gradation values corrected by the calibration data 245c as the gradation values in the three-dimensional coordinates. Then, the control unit 240 regards the colors of the three-dimensional coordinates indicated by the three-dimensional image data 245b as the gradation values, and controls the display 230 so that the three-dimensional images (tomographic images Iov, Ioh and Ior) are displayed thereon.

As a result, although not shown in FIG. 4, the tomographic images Iov, Ioh and Ior are colored and displayed. In the correspondence definition data 245d, the correspondence with the two-dimensional coordinates does not have to be defined for all of the three-dimensional image for expressing the three-dimensional image. For example, for a site outside the visual field of the color camera, a site that is transparent and thus is not colored, a site that is located on the back side of the eye E to be examined and thus is not photographed with the color camera, etc., the correspondence definition data 245d may not be defined. In this case, the control unit 240 can adopt a configuration in which a site where the correspondence definition data 245d does not exist is displayed with a color that can be expressed by the gradation value indicated by the three-dimensional image data 245b (that is, a grayscale image). Further, the colored site (predetermined site) is the iris, the surface of the anterior segment other than the iris and the cornea, the eyelid, or the like.

Various modes can be adopted as the display mode of the three-dimensional image. The section is not limited to the example shown in FIG. 4, and, of course, any section can be selected by the examiner's designation. Also, a section parallel to the Z direction may be selected. Furthermore, a projection view when the section is viewed from a certain direction (for example, a view in which information on a predetermined range in the Z direction is projected on the section parallel to the Z direction) may be displayed. Furthermore, a three-dimensional model may be generated based on the three-dimensional image, and a view when the three-dimensional model is viewed from an arbitrary direction may be colored and displayed. As such an example, for example, a three-dimensional model displayed by volume rendering or surface rendering may be colored and displayed.

According to the above configuration, by associating a local structure of the eye E to be examined, which is specified based on the three-dimensional image obtained by optical coherence tomography, with the color developing in the front of the eye E, the local structure can be colored. Therefore, the present embodiment can be used for various purposes of observing the anterior segment using colors, for example, evaluating the colors and forms of affected areas, the distribution of blood vessels, etc. in order to perform differential diagnosis, to grasp the condition, and to perform follow-up observation. There are a wide variety of diseases, including allergic conjunctival disease with conjunctival hyperemia, corneal dystrophy that develops in association with infectious keratitis with corneal opacification and gene abnormality, corneal epithelial disorder caused by dry eye and the like, pterygium in which part of the conjunctival tissue extends to the cornea with blood vessels, tumors that develop in the iris, conjunctiva, and eyelid, retinoblastoma that can be observed from the pupil, and vascular glaucoma neovascularization in which new blood vessels appear in the iris.

The colored anterior segment also facilitates observation after corneal transplantation or amniotic membrane transplantation, functional evaluation of the filtration bleb after filtration bleb surgery in glaucoma, follow-up observation of tube-shunt implant surgery, and the like. Furthermore, if coloring is performed as in the present embodiment, the probability of correctly grasping the pathological condition and not overlooking slight changes increases. Further, for each disease, clinical evaluation criteria such as the degree of hyperemia, the color of the affected area, and the spread of the lesion may be provided as indexes of the classification, severity, and malignancy. However, in the present embodiment, the reproducibility of colors is ensured by the calibration data. Therefore, classification and determination of severity/malignancy can be performed correctly, and the possibility of misdiagnosis or oversight can be reduced.

Further, as a determination method for classification and determination of severity/malignancy, there is often used a method of visually comparing a color image of the anterior segment of the eye E to be examined with a color image as a sample of a representative case prepared for each severity, a schema with comments, or the like to judge the grade to which the classification and determination of severity/malignancy belongs. Even in this case, since color reproducibility is ensured in the present embodiment, quantitative evaluation based on various color components is possible, and thus more objective and stable evaluation is possible.

Furthermore, in recent years, in the production of artificial eyes using a 3D printer, attempts have been started to use slit-lamp microscope color images of actual eyes. In order to match the color and texture of the iris and blood vessels of the conjunctiva printed on the artificial eyes with those of the actual eyes, it is preferable that the color reproducibility of the color images be ensured. Furthermore, color images can capture only information on the surfaces of the eyes. However, by being combined with three-dimensional images including the depth direction of lesions or OCT angiography images known as three-dimensional non-invasive angiography technique by OCT, the color images can capture the degree of infiltration into the internal tissue, the three-dimensional morphology, the characteristics of blood vessel invasion into the affected site inside the tissue, and the like, thereby carrying out a more accurate diagnosis.

(3) Calibration Data Generation Process

Figure 5A:
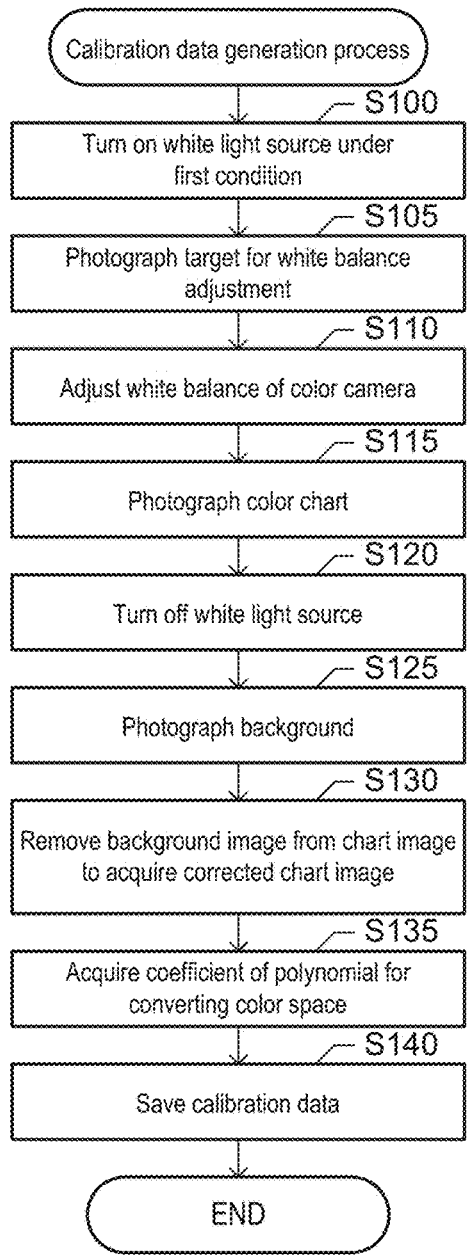
FIG. 5A is a flowchart of calibration data generation process.

Next, the process of generating the calibration data used for ensuring the color reproducibility of the two-dimensional image captured with the color camera will be described in detail. FIG. 5A is a flowchart of the calibration data generation process. In the present embodiment, the calibration data generation process is performed before the shipment of the optical coherence tomographic device 1. When the calibration data generation process is started, the white light sources 205, 205 are turned on under first conditions (step S100). That is, an operator of the calibration data generation sets light emission conditions to the first conditions via an input unit (not shown) and gives an instruction to turn on the white light sources 205, 205. As a result, the control unit 240 causes the white light sources 205, 205 to be turned on under the set first conditions. The first conditions are the same as the conditions when the eye E to be examined is illuminated for capturing the two-dimensional image data 245a with the color camera, and, in the present embodiment, are conditions under which white light having a predetermined bright degree (luminous intensity, brightness, illuminance, etc.) at a color temperature of 5500 K is output from the white light sources 205, 205.

Next, the target for white balance adjustment is photographed (step S105). Specifically, the operator sets the target for white balance adjustment at a position where the eye E to be examined is to be arranged when photographed. The target for white balance adjustment is an achromatic color sample prepared in advance, and is a color sample of light gray close to white in the present embodiment. The operator gives a photographing instruction through an input unit (not shown) with the target for white balance adjustment set. As a result, the control unit 240 controls the area sensor 208 of the scanning-alignment optical system 200 to acquire an image of the target for white balance adjustment, using the function of the two-dimensional image acquisition unit 240a.

Next, the control unit 240 adjusts the white balance of the color camera (step S110). That is, the control unit 240 adjusts the gradation values indicating the colors of the target for white balance adjustment captured in step S105 to predetermined gradation values. Various techniques may be used as the white balance adjustment method. For example, the gain of analog-to-digital conversion can be adjusted after the intensity of light of each of RGB are detected, and the RAW data which is an output value of a photoelectric conversion element for detecting each RGB color can be adjusted. In any case, the gradation values of RGB to be detected as the colors of the target for white balance adjustment are predetermined, and the control unit 240 adjusts the gain, adjusts the conversion formula for conversion from the RAW data to the RGB gradation values, or the like, thereby performing white balance adjustment. When the white balance adjustment is performed in this way, the white balance setting is maintained until the white balance adjustment is performed later again.

Next, the color chart is photographed (step S115). That is, the operator sets the color chart at the position where the eye E to be examined is to be arranged when photographed. The color chart is a color sample having a plurality of color patches, and has predetermined chromatic color patches and achromatic color patches in order to cover colors over the entire color space. The operator gives a photographing instruction through an input unit (not shown) with the color chart set.

As a result, the control unit 240 controls the area sensor 208 of the scanning-alignment optical system 200 to acquire a chart image which is an image of the color chart, using the function of the two-dimensional image acquisition unit 240a. Since the color chart includes a plurality of color patches (for example, 24), a chart image is acquired for each color patch.

In the present embodiment, it is assumed that the color chart and the eye E to be examined are photographed under indoor illumination. In this case, the influence of the indoor illumination forms the background of the image. The indoor illumination generally differs depending on the photographing environment. Therefore, if process is performed in a state in which the background is included, the color reproducibility may deteriorate. Therefore, in the present embodiment, process for removing the background is performed.

Specifically, the control unit 240 turns off the white light sources 205, 205, using the function of the two-dimensional image acquisition unit 240a (step S120). At this time, the indoor illumination is maintained to be turned on. Next, the background is photographed (step S125). Specifically, the control unit 240 controls the area sensor 208 of the scanning-alignment optical system 200 to photograph the color chart set in step S115 and acquire the resultant image as a background image, using the function of the two-dimensional image acquisition unit 240a. Note that when the background image is captured, the exposure adjustment is not performed, and capturing is performed under the same exposure conditions as in step S115.

Next, the control unit 240 removes the background image from the chart image to acquire a chart image after the correction (step S130). That is, the control unit 240 removes each gradation value of the background image acquired in step S125 from each gradation value of the chart image acquired in step S115 to acquire the resultant image as a chart image after the correction. According to the above configuration, the influence of indoor illumination can be removed from the chart image.

Next, the control unit 240 acquires a coefficient of a polynomial for converting the color space (step S135). That is, in the present embodiment, the gradation values of the image captured with the color camera indicate the colors expressed in the device-dependent color space. Therefore, when the output on the display 230 is performed using the gradation values of the chart image, it is not ensured that the colors of the color patches match the actual colors. Therefore, in the present embodiment, it is assumed that the gradation values of the color patches in the chart image are converted into the gradation values in the reference color space (sRGB) by using cubic polynomials.

In order to enable the conversion by using such cubic polynomials, the control unit 240 acquires the coefficients of the cubic polynomials based on the RGB gradation value of each color patch obtained as the chart image and the sRGB gradation value known as the color of each color patch. Specifically, the cubic polynomials are expressed in the following formulas (1) to (3).

<IMG SRC="TO19004JPformula-1.bmp"> Mathematical Formula 1

Formula (1) is a conversion formula for calculating the R gradation value in the sRGB color space from the RGB gradation values of the two-dimensional image data 245a, and formula (2) is a conversion formula for calculating the G gradation value in the sRGB color space from the RGB gradation values of the two-dimensional image data 245a. Formula (3) is a conversion formula for calculating the B gradation value in the sRGB color space from the RGB gradation values of the two-dimensional image data 245a. Further, the symbol n in each formula indicates the number of the color patch. Therefore, if there are 24 color patches, n is an integer value of 1 to 24.

With the above indication, in each formula, $(R_n, G_n, B_n)$ means gradation values obtained by photographing the n-th color patch with the color camera. In each formula, 0-order to third-order terms are included for each gradation value, and there are coefficients $\alpha_0$ to $\alpha_9$ by which each term is multiplied. In the present embodiment, these coefficients are different for R, G, and B, respectively. So, the symbols r, g, and b are attached to each of formulas (1) to (3) in order to distinguish the coefficients from each other in each of formulas (1) to (3).

When there are N color patches, N formulas are obtained for each of formulas (1) to (3). For example, if the R component of the sRGB gradation values of the first color patch is $R_{s1}$ and the gradation values captured with the color camera are $(R_1, G_1, B_1)$, the left side is $R_{s1}$, and $(R_1, G_1, B_1)$ is substituted into the right side. One formula in which coefficients $\alpha_{r0}$ to $\alpha_{r9}$ are unknown is obtained. If this substitution is performed for the N color patches, N formulas are obtained. Therefore, the control unit 240 specifies the coefficients $\alpha_{r0}$ to $\alpha_{r9}$ from the N formulas by the least square method or the like. Similarly, if the coefficients are also determined for formula (2) and formula (3), formulas (1) to (3) for converting arbitrary gradation values obtained by photographing with the color camera into sRGB gradation values are obtained. When the polynomial coefficients are obtained in the way as described above, the control unit 240 saves the calibration data (step S140). Specifically, the control unit 240 causes the coefficient values acquired in step S135 to be recorded as the calibration data 245 in the storage medium 245c.

(4) Photographing Process

Next, photographing processes of the two-dimensional image and the three-dimensional image will be described. The photographing processes are executed in accordance with an instruction from the examiner, in a state where the eye E to be examined is arranged in front of the inspection window and the eye E to be examined exists in the visual field of the color camera and at a position where it can be photographed by the OCT interference system 100. When the photographing process is started, the white light sources 205, 205 are turned on under second conditions (step S200). That is, the examiner sets the light emission conditions to the second conditions via an input unit (not shown) and gives an instruction to turn on the white light sources 205, 205. As a result, the control unit 240 causes the white light sources 205, 205 to be turned on under the set second conditions.

The second conditions are light emission conditions at the time of alignment by the scanning-alignment optical system 200 and live display of a two-dimensional image captured with the color camera, and are preset. In the present embodiment, the color temperature is not limited, but is preferably close to the color temperature under the first conditions which are the illuminating conditions for the two-dimensional image, in order to bring the colors of the image live-displayed to the colors of the two-dimensional image captured after the live display. However, it is preferable that the bright degree (luminous intensity, brightness, illuminance, etc.) of the white light sources 205, 205 be smaller than that in the first conditions.

That is, in step S200 and the subsequent steps, illumination is performed over a period of time for a relatively time-consuming process such as alignment or optical coherence tomography. Thus, it is preferable that the bright degree (luminous intensity, brightness, illuminance, etc.) be smaller than that in the first conditions and also be not excessively dark, in order to suppress increase in blinking, unstable movement of the eye E to be examined, and excessive contraction of the pupil. In addition, the two-dimensional image captured in the state of illumination under the first conditions is always under fixed conditions because it is necessary to ensure color reproducibility, and illumination must be performed under the same conditions as the conditions when the calibration data 245c is prepared. However, it is not necessary to strictly obtain color reproducibility for live display and the like. Therefore, under the second conditions, the bright degree (luminous intensity, brightness, illuminance, etc.) of white light may be smaller than that under the first conditions. For example, JIS Z9110, which is prescribed for the purpose of promoting the formation of a comfortable working environment, stipulates that the illuminance suitable for a meeting place or an office is about 200 to 2000 1x. In addition, according to "Changes in eyelid fissure height and pupillary size induced by different illuminances" (Japanese Journal of Clinical Ophthalmology 50 (4): 769-722, 1999), the pupil diameter stably decreases with increase of the illuminance when the illuminance is 200 1x to 2000 1x, but unstably changes with increase of illuminance when the illuminance exceeds 2000 1x. Therefore, it is preferable that the illuminance of white light be 200 1x to 2000 1x under the second conditions, and that the illuminance under the first conditions be greater than the illuminance under the second conditions selected from the range. Of course, the first conditions and the second conditions may be the same as long as it is not necessary to consider the influence of the increase in blinking.

Next, the control unit 240 starts optical coherence tomography and live display of the color image (step S205). That is, the control unit 240 controls the anterior segment photographing system (the area sensor 208 and the like) that functions as the color camera to acquire a two-dimensional image of the eye E to be examined, using the function of the two-dimensional image acquisition unit 240*a*. At this time, the control unit 240 may allow the two-dimensional image data 245*a* indicating the captured two-dimensional image to be recorded in the storage medium 245 or stored in a RAM (not shown). When the two-dimensional image is acquired, the control unit 240 controls the display 230 to display the two-dimensional image, using the function of the display control unit 240*d*. The mode of the live display is not limited, but display such as the two-dimensional image Ie shown in FIG. 4 can be adopted.

Further, the control unit 240 controls the OCT interference system 100, the scanning-alignment optical system 200 (such as the galvanometer scanner 202), and the k-clock generating interference optical system 400 to acquire the measurement interference signal, using the function of the three-dimensional image acquisition unit 240*b*. The control unit 240 performs process such as inverse Fourier transform on the measurement interference signal and acquires a tomographic image of the anterior segment Ec along the scanning line. The control unit 240 limits the scanning direction of the galvanometer scanner 202 to a section for obtaining a tomographic image of a display target, and acquires a tomographic image of the section of the display target.

At this time, the control unit 240 may allow the captured tomographic image data to be recorded in the storage medium 245 or stored in a RAM (not shown). When the three-dimensional image is acquired, the control unit 240 controls the display 230 to display the three-dimensional image, using the function of the display control unit 240*d*. The mode of live display is not limited, but for example, displays such as the tomographic images Iov, Ioh, and Ior shown in FIG. 4 can be adopted. The execution of the live display in step S205 is started at a stage before the alignment is completed. Therefore, at the initial stage, the central portion of the cornea of the eye E to be examined may not exist in the center of the live-displayed image.

Next, the control unit 240 carries out alignment (step S210). That is, the control unit 240 controls the XY-position detection light source 216 to output alignment light for detection of the position in the X-Y direction. The alignment light is reflected on the corneal surface so as to form a bright spot image inside the conical apex of the eye E to be examined, and the reflected light is detected by the two-dimensional position sensor 218. The control unit 240 specifies the position of the bright spot, that is, the position of the conical apex (the positions in the X and Y directions) based on the output signal of the two-dimensional position sensor 218. Furthermore, the control unit 240 obtains the amounts of positional deviation in the X and Y directions, which are necessary to match the bright spot indicating the conical apex with a predetermined position of the imaging element. Then, the control unit 240 moves the device main body in the direction opposite to the positional deviation so that the positional deviation amounts become zero.

Further, the control unit 240 controls the Z-position detection light source 219 to cause the eye E to be examined to be irradiated with detection light (slit light or spot light) from an oblique direction. As a result, the reflected light reflected on the cornea is incident on the line sensor 221 via the imaging lens 220. The control unit 240 detects the Z-direction position of the eye E to be examined based on the output signal of the line sensor 221. Further, the control unit 240 obtains the amount of positional deviation in the Z direction, which is necessary to match the reflected light from the cornea with a predetermined position of the line sensor 221. Then, the control unit 240 moves the device main body in the direction opposite to the positional deviation so that the positional deviation amount becomes zero.

Since the movements in the XYZ directions as described above are performed for each predetermined movement distance, the alignment is generally completed by repeating the alignment. Therefore, the control unit 240 determines whether or not the alignment is completed (step S215). That is, the control unit 240 determines that the alignment has been completed when the deviation amounts become 0 (or the absolute values of the deviation amounts are equal to or less than the threshold values). When it is not determined in step S215 that the alignment has been completed, the control unit 240 repeats the processes in step S210 and the subsequent steps.

When it is determined in step S215 that the alignment has been completed, the control unit 240 performs eye tracking (step S220). The eye tracking is an operation that changes the capturing position of the three-dimensional image according to the position displacement of the eye to be examined Specifically, a characteristic point of the eye to be examined (for example, a bright spot or a site having predetermined characteristics) is detected by the two-dimensional position sensor 218 or the area sensor 208 to specify the position change of the eye to be examined after the alignment. Then, the control unit 240 performs feedback control for correcting the scanning position of the galvanometer scanner 202 so that the position change is canceled. As a result, it is possible to acquire a three-dimensional image equivalent to that when there is no change in the position of the eye to be examined after completion of the alignment.

Next, the control unit 240 acquires a three-dimensional image using the function of the three-dimensional image acquisition unit 240*b* (step S225). That is, the control unit 240 controls the OCT interference system 100, the scanning-alignment optical system 200 (such as the galvanometer scanner 202), and the k-clock generating interference optical system 400 to acquire the measurement interference signal, using the function of the three-dimensional image acquisition unit 240*b*. The control unit 240 performs process such as inverse Fourier transform on the measurement interference signal and acquires a tomographic image of the anterior segment Ec along the scanning line.

The control unit 240 changes the scanning direction of the galvanometer scanner 202 to acquire tomographic images for a plurality of sections covering the entire anterior segment of the eye E to be examined. Then, the control unit 240 generates a three-dimensional image based on the plurality of tomographic images obtained, and records the three-dimensional image data 245*b* indicating the obtained three-dimensional image in the storage medium 245. When the three-dimensional image is acquired, the control unit 240 ends the eye tracking (step S230).

Next, the white light sources 205, 205 are turned on under the first conditions (step S235). That is, the examiner sets the light emission conditions to the first conditions via an input unit (not shown) and gives an instruction to turn on the white light sources 205, 205. As a result, the control unit 240 turns on the white light sources 205, 205 under the set first conditions (color temperature of 5500 K, and predetermined bright degree (luminous intensity, brightness, illuminance, etc.)).

Next, the control unit 240 captures an image of the eye E to be examined using the function of the two-dimensional image acquisition unit 240a (step S240). That is, the control unit 240 controls the anterior segment photographing system (the area sensor 208 and the like) that functions as the color camera to acquire an image of the eye E to be examined, using the function of the two-dimensional image acquisition unit 240a.

Next, the control unit 240 executes process for removing the background. Specifically, the control unit 240 turns off the white light sources 205, 205, using the function of the two-dimensional image acquisition unit 240a (step S245). At this time, the indoor illumination is maintained in the on state. Next, the background is photographed (step S250). Specifically, the control unit 240 controls the area sensor 208 of the scanning-alignment optical system 200 to photograph the eye E to be examined and acquire the resultant image as a background image, using the function of the two-dimensional image acquisition unit 240a. Note that when the background image is captured, the exposure adjustment is not performed, and capturing is performed under the same exposure conditions as in step S240.

Next, the control unit 240 removes the background image from the image of the eye E to be examined to acquire a two-dimensional image, using the function of the two-dimensional image acquisition unit 240a (step S255). That is, the control unit 240 removes each gradation value of the background image acquired in step S250 from each gradation value of the image of the eye E to be examined acquired in step S240 to acquire the resultant image as a two-dimensional image after the correction. Then, the control unit 240 records the two-dimensional image data 245a indicating the two-dimensional image in the storage medium 245. According to the above configuration, the influence of indoor illumination can be removed from the two-dimensional image of the eye E to be examined.

Next, the control unit 240 executes color calibration using the function of the two-dimensional image acquisition unit 240a (step S260). That is, the control unit 240 refers to the calibration data 245c recorded in the storage medium 245 and corrects the gradation values of respective two-dimensional coordinates indicated by the two-dimensional image data 245a. For example, when the gradation values at certain coordinates (u, v) are $(R_i, G_i, B_i)$, the red component $R_o$ of the corrected gradation values $(R_o, G_o, B_o)$ is a value obtained by substituting $(R_i, G_i, B_i)$ into formula (1). Further, the green component $G_o$ after the correction is a value obtained by substituting $(R_i, G_i, B_i)$ into formula (2), and the blue component $B_o$ after the correction is a value obtained by substituting $(R_i, G_i, B_i)$ into formula (3). When the correction is performed for all the pixels of the two-dimensional image, the control unit 240 updates the storage medium 245 with the two-dimensional image data 245a indicating the two-dimensional image after the correction. According to the above process, it is possible to generate the two-dimensional image data 245a in which the colors are described without depending on the output device, and to ensure the color reproducibility.

(4-1) Correspondence Definition Data Generation Process

Figure 5B:
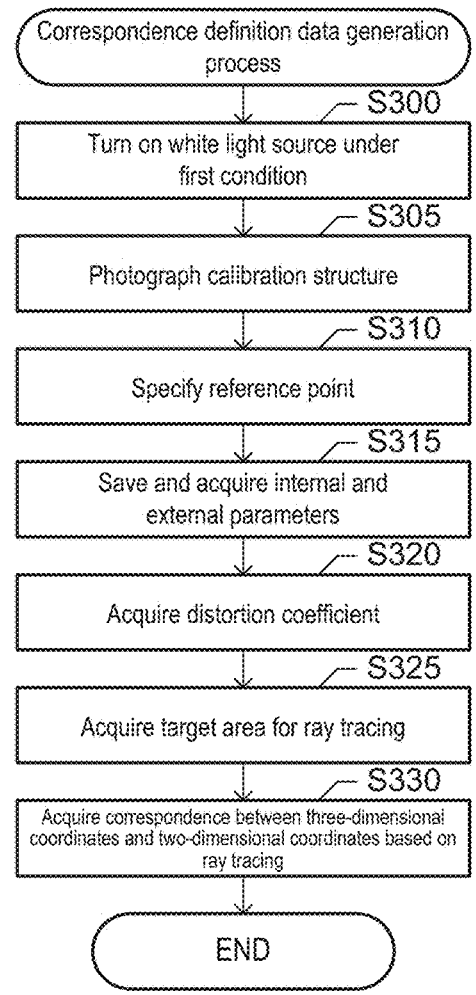
FIG. 5B is a flowchart of correspondence definition data generation process.

Next, the control unit 240 executes correspondence definition data generation process using the function of the correspondence definition data generation unit 240c (step S265). FIG. 5B is a flowchart showing the correspondence definition data generation process. In the correspondence definition data generation process, the control unit 240 turns on the white light sources under the first conditions (step S300). That is, the control unit 240 turns on the white light sources 205, 205 under the same conditions as those when the two-dimensional image is captured with the color camera.

Next, a calibration structure is photographed (step S305). The correspondence definition data is data that defines the correspondence between the three-dimensional coordinates of a three-dimensional image and the two-dimensional coordinates of a two-dimensional image. Therefore, in the present embodiment, a configuration is adopted in which the correspondence is defined by actually photographing the calibration structure with the color camera.

Figure 5C:
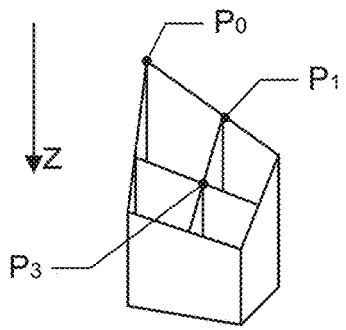
FIG. 5C is a diagram showing a calibration structure.

The calibration structure is a three-dimensional structure for clarifying the correspondence between the three-dimensional coordinates of the three-dimensional image and the two-dimensional coordinates of the two-dimensional image, for example, a structure as shown in FIG. 5C. The structure shown in FIG. 5C has a shape obtained by obliquely cutting a rectangular parallelepiped having a distorted cavity, and also has a shape such that the inner cavity is partitioned by a plurality of wall surfaces. The structure is arranged in front of the inspection window provided in the front surface of the device main body so that the inner cavity is included in the visual field of the color camera. Therefore, the Z direction shown in FIG. 2 is a direction from the top to the bottom in FIG. 5C.

The calibration structure is configured to have such a shape that a specific position of the calibration structure is apparent in the image when viewed from such a direction. For example, in the structure shown in FIG. 5C, the positions of intersection points ($P_1$, $P_2$, $P_3$, etc.) between the respective wall surfaces can be easily specified in the image when the structure is photographed as a three-dimensional image or a two-dimensional image. Here, such points are referred to as reference points.

In the present embodiment, a two-dimensional image and a three-dimensional image are captured with the calibration structure set in the device main body. That is, the control unit 240 controls the anterior segment photographing system (the area sensor 208 and the like) that functions as the color camera to acquire a two-dimensional image of the calibration structure, using the function of the two-dimensional image acquisition unit 240a. Also, the control unit 240 controls the OCT interference system 100, the scanning-alignment optical system 200 (such as the galvanometer scanner 202), and the k-clock generating interference optical system 400 to acquire a three-dimensional image of the calibration structure, using the function of the three-dimensional image acquisition unit 240b.

Next, the control unit 240 specifies the reference points (step S310). That is, the control unit 240 specifies the reference points based on the two-dimensional image captured in step S305, and specifies the two-dimensional coordinates of the reference points. Further, the control unit 240 specifies the reference points based on the three-dimensional image captured in step S305, and specifies the three-dimensional coordinates of the reference points. Note that the reference points may be specified by various techniques. Each of the reference points may be specified by an input by the examiner, or specified based on a characteristic amount indicating a characteristic of the reference point, which is acquired from the two-dimensional image and the three-dimensional image, respectively. In any case, for each of the plurality of reference points, the two-dimensional image and the three-dimensional image for the same reference point are associated with each other.

As a result, the three-dimensional coordinates of the three-dimensional image are associated with the two-dimensional coordinates of the two-dimensional image, at the positions where the plurality of reference points are photographed. Therefore, in the present embodiment, the correspondences for a larger number of coordinates are defined from these correspondences. For this purpose, the control unit 240 acquires an internal parameter and an external parameter (step S315). Specifically, when the color camera is used to photograph the subject in the visual field so that an image is obtained, the relationship between the coordinates of the subject and the coordinates of the image can be described based on a known relational formula (4).

<IMG SRC="TO19004JPformula-2.bmp"> Mathematical Formula 2

Here, the three-dimensional coordinates (X, Y, Z) are coordinates that describe a three-dimensional position in the three-dimensional image data 245b, and the two-dimensional coordinates (u, v) are coordinates that describe a two-dimensional position in the two-dimensional image data 245a. In formula (4), the column vector (X, Y, Z, 1) including the three-dimensional coordinates (X, Y, Z) is multiplied by two types of matrices. The matrix of 3 rows and 3 columns represents the internal parameter of the color camera; $(c_x, c_y)$ represents the principal point (in the present embodiment, the center of the two-dimensional image); and $f_x$ and $f_y$ are each a focal length represented in pixel units. On the other hand, the matrix of 3 rows and 4 columns in formula (4) represents the external parameter, and represents the rotation ($r_{11}$ to $r_{33}$) and translation ($t_1$ to $t_3$) for converting the three-dimensional coordinates viewed from the camera into the three-dimensional coordinates in which the results of the optical coherence tomography are described.

The internal parameter is a parameter indicating the characteristics of the optical system of the color camera, and is determined based on the optical system of the color camera, that is, the anterior segment photographing system. In the present embodiment, the internal parameter 245e is recorded in the storage medium 245 in advance (internal parameter 245e). The external parameter is a parameter for associating the world coordinate system outside the color camera with the three-dimensional coordinate system viewed from the color camera, and is determined based on the relationship between the eye E to be examined and the color camera. In the present embodiment, The external parameters are specified in advance based on the relationship between the optical system of the color camera and the space where the eye E to be examined, which serves as the subject, is arranged, so that the world coordinate system matches the three-dimensional coordinate system used in the three-dimensional image obtained by optical coherence tomography. In the present embodiment, the external parameter is also determined in advance and recorded in the storage medium 245 (external parameter 245f).

According to the internal parameter 245e and the external parameter 245f as described above, the three-dimensional coordinates indicating the position of each site of the eye E to be examined photographed by optical coherence tomography can be associated with the two-dimensional coordinates indicating the position of the eye E to be examined on the two-dimensional image captured with the color camera. However, since the lenses of the color camera (the objective lens 204 and the imaging lens 207) have various distortions, formula (4) is transformed so that the results obtained by the external parameter 245f may include the effect of distortion, in the present embodiment.

Specifically, the formula for transforming the three-dimensional coordinates (X, Y, Z) by the external parameter 245f is expressed as the following formula (5).

<IMG SRC="TO19004JPformula-3.bmp"> Mathematical Formula 3

In the formula, R is a matrix indicating the rotation ($r_{11}$ to $r_{33}$) of the external parameter 245f, and t is a vector indicating the translation ($t_1$ to $t_3$) of the external parameter 245f.

Then, the formulas in which the influence of the distortion is incorporated are expressed as the following formulas (6) to (12).

<IMG SRC="TO19004JPformula-4.bmp"> Mathematical Formula 4

That is, when the coordinates (x, y, z) obtained by formula (5) are substituted into formulas (6) and (7), the coordinates (x', y') are obtained. When the obtained coordinates (x', y') are substituted into formulas (8) and (9), and formula (10) is utilized, the coordinates (x", y") are obtained. Then, the obtained coordinates (x", y") are substituted into formulas (11) and (12), and calculation is performed based on the internal parameter 245e, the two-dimensional coordinates (u, v) are obtained.

The three-dimensional coordinates (X, Y, Z) can be converted into the two-dimensional coordinates (u, v) in the way as described above. Therefore, when distortion coefficients $k_1$, $k_2$, $p_1$ and $p_2$ that are unknown coefficients included in formulas (6) to (12) are specified, the correspondence between the three-dimensional coordinates of the three-dimensional image and the two-dimensional coordinates of the two-dimensional image is defined. Therefore, the control unit 240 acquires the distortion coefficients $k_1$, $k_2$, $p_1$ and $p_2$ based on the correspondence between the two-dimensional image and the three-dimensional image for the plurality of reference points specified in step S310 (step S320). For example, the control unit 240 specifies the equations for solving the distortion coefficients $k_1$, $k_2$, $p_1$ and $p_2$ from formulas (6) to (12) using the correspondence with respect to the reference points to specify the distortion coefficients. Of course, the solution may be calculated so as to be close to the true values of the distortion coefficients $k_1$, $k_2$, $p_1$ and $p_2$ by utilizing the correspondence with respect to a larger number of reference points.

In any case, when the distortion coefficient is acquired, the control unit 240 records the information on formulas (6) to (12) including the values of the distortion coefficients, as the correspondence definition data 245d, in the storage medium 245. In addition, in the present embodiment, the sites (predetermined sites) to be colored are predetermined. Therefore, the control unit 240 generates the correspondence definition data 245d for the predetermined sites such as iris, the anterior segment surface other than the iris and the cornea, the eyelids, etc.

The distortion coefficients and formulas (6) to (12), as described above, can be used to define the correspondence between the three-dimensional coordinates of the three-dimensional image of the eye E to be examined and the two-dimensional coordinates of the two-dimensional image thereof. However, the cornea of the eye E to be examined, which functions as a lens, is not considered in this correspondence. Therefore, if the refraction by the cornea is not considered, the three-dimensional coordinates of the three-dimensional image of the eye E to be examined can be associated with the two-dimensional coordinates of the two-dimensional image.

In the present embodiment, in consideration of the refraction by the cornea, the correspondence is defined so as to be more faithful to the actual appearance of the eye E to be examined Specifically, for the iris existing on the back side of the cornea, the ray tracing is taken into consideration to define the correspondence. For this purpose, the control unit 240 acquires the target area for ray tracing (step S325). In the present embodiment, a site that is affected by the refraction of the cornea and is not transparent, i.e., the iris, is the target area for ray tracing. Therefore, the control unit 240 extracts, from the two-dimensional image data 245a and the three-dimensional image data 245b, a portion where the image of the iris is captured, and sets it as a target area for ray tracing. Note that various techniques may be used as the technique of extracting the image of the iris, and, for example, the control unit 240 may accept the range designation by the examiner, or specify the target area by extracting a characteristic amount indicating a characteristic of the iris from the three-dimensional image and the two-dimensional image, respectively.

When the target area is acquired, the control unit 240 acquires the correspondence between the three-dimensional coordinates and the two-dimensional coordinates, for the target area, based on ray tracing (step S330). That is, the control unit 240 performs ray tracing on an arbitrary portion of the iris which is included in the target area and is not transparent.

Figure 7:
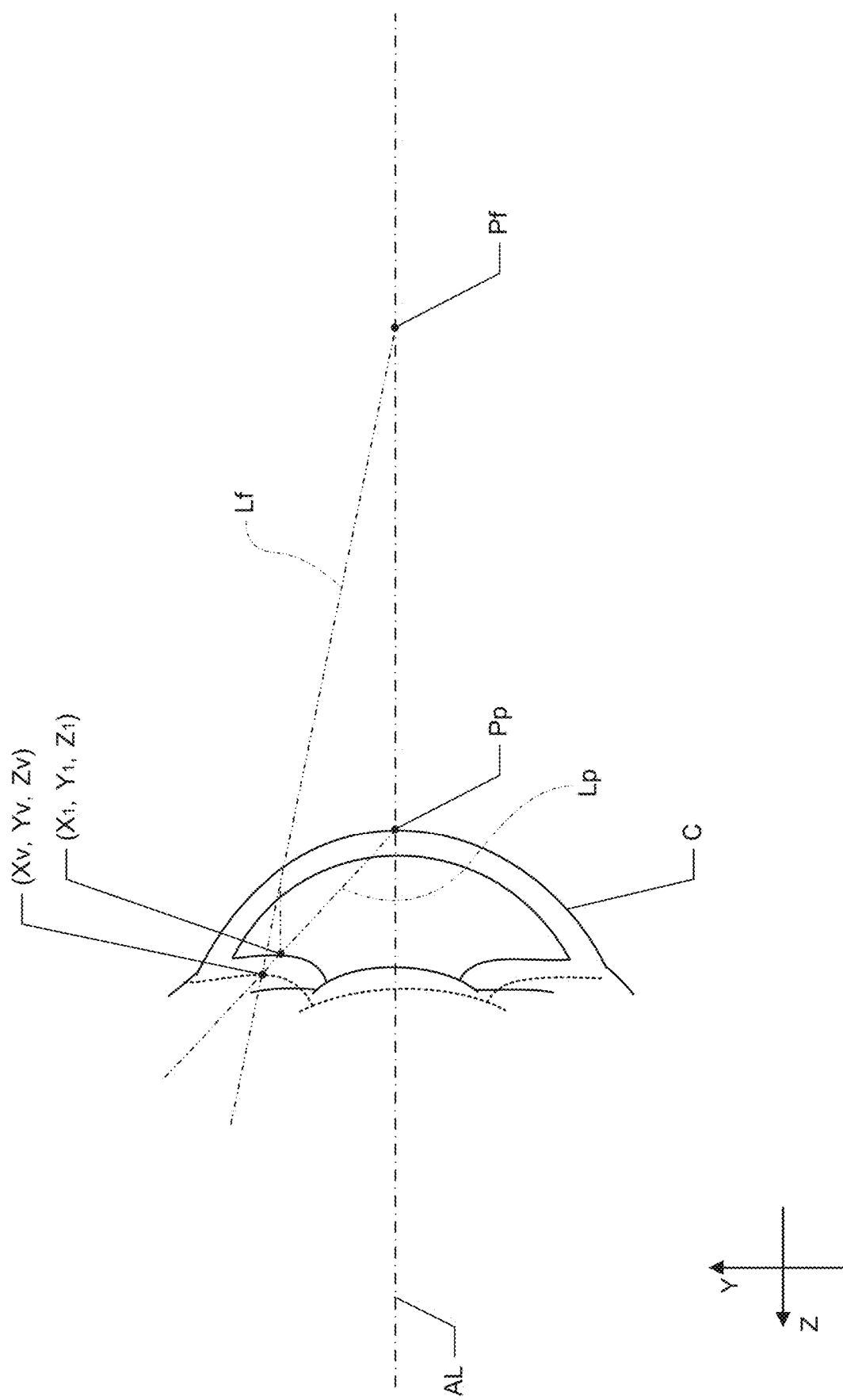
FIG. 7 is a diagram illustrating an example of ray tracing.

FIG. 7 is a diagram illustrating an example of ray tracing. In FIG. 7, the structure of a cornea C and its periphery of the eye E to be examined is shown, with a plane which passes through the corneal center and is parallel to the Z and Y directions being as a section. Note that, in FIG. 7, an optical axis AL which passes through the corneal apex and is parallel to the Z direction is shown by a dashed-dotted line, and that a virtual ray is shown by a dashed-two dotted line.

The control unit 240 can specify the structure of the eye E to be examined on the section as shown in FIG. 7 by the three-dimensional image data 245b. The control unit 240 determines a focus position Pf and a principal point position Pp on the section based on the shape of the cornea specified by the three-dimensional image data 245b.

The focus position Pf can be defined, for example, by specifying an intersection between the optical axis AL and a ray imaginarily assumed at the time of performing ray tracing on the three-dimensional coordinates $(X_1, Y_1, Z_1)$, the ray extending from the three-dimensional coordinates $(X_1, Y_1, Z_1)$ to the direction parallel to the optical axis (Z direction), and, when reaching the cornea, being refracted by the refractive power of the cornea, and intersecting with the optical axis AL. The refraction at the cornea may be regarded as occurring once with a predetermined refraction index. Or, the refraction at the cornea may be regarded as occurring once on the back surface and the front surface, respectively, of the cornea, with the refraction indexes on the respective surfaces being different predetermined values.

The principal point position Pp can be defined as, for example, an intersection between the optical axis AL and the corneal anterior surface (corneal apex). That is, it is considered that the principal point position of the cornea is almost equal to the corneal anterior surface (for example, <Lecture> Fundamentals of Eye Optics (Vision Society of Japan), Journal "VISION", Vol. 1 No. 1 (January 1989))). Therefore, the principal point position Pp can be defined, for example, by specifying an intersection between the front surface of the cornea C indicated by the three-dimensional image data 245b and the optical axis AL.

Of course, the methods of acquiring the focus position Pf and the principal point position Pp are examples, and these points may be acquired by other techniques. For example, the principal point position Pp may be calculated from the general formula of the principal point position Pp specified based on ray tracing. Specifically, the principal point position Pp can be acquired by using the following parameters. Curvature radius of corneal anterior surface=$r_1$; curvature radius of corneal posterior surface=$r_2$, refractive index of air=$n_1$, refractive index of corneal stroma=$n_2$, refractive index of anterior chamber water=$n_3$, thickness of corneal center=d, refractive index of corneal anterior surface=$D_1$, refractive index of corneal posterior surface=$D_2$, and total refractive index of cornea=$D_t$.

Incidentally, the curvature radius $r_1$ of the corneal anterior surface and the curvature radius $r_2$ of the corneal posterior surface can be acquired by the control unit 240 specifying the corneal anterior and posterior surfaces, respectively, based on the characteristic amount and the like, based on the three-dimensional image data 245b, and calculating the centers of curvature based on at least three points on the respective surfaces and calculating the distances to the respective surfaces. The thickness d of the corneal center can be acquired by the control unit 240 specifying the distance between the corneal anterior surface and the corneal posterior surface on the optical axis AL, for example. As the refractive index n of the air, the refractive index $n_2$ of the corneal stroma, and the refractive index $n_3$ of the anterior chamber water, known values (for example, 1.0, 1.376, and 1.336, respectively) can be used.

The refractive index $D_1$ of the corneal anterior surface is $D_1 = (n_2 - n_1)/r_1$ The refractive index $D_2$ of the corneal posterior surface is $D_2 = (n_3 - n_2)/r_2$ The total refractive index $D_t$ of the cornea is $D_t = D_1 + D_2 - (d/n_2) \cdot D_1 \cdot D_2$ The distance from the corneal anterior surface to the image-side principal point position is e'+d as follows.

$$e' + d = -d \cdot n_3 \cdot D_1/(n_2 \cdot D_t) + d$$

Based on the thus-calculated image-side principal point position, the control unit 240 may regard the position of the distance e'+d from the intersection between the corneal anterior surface and the optical axis AL to the image side as the principal point position Pp.

When the focus point Pf and the principal point position Pp are determined, the coordinates (Xv, Yv, Zv) of the intersection of a line obtained by extending a ray Lf to the back side of the eye E to be examined and the line Lp can be defined as the position of a virtual image. Here, the ray Lf is the light refracted by the cornea after traveling in parallel to the Z direction from the three-dimensional coordinates (X1, Y1, Z1) and towards to the focus point Pf. And the line Lp is the line that connects the principal point position Pp and the three-dimensional coordinates (X1, Y1, Z1). In FIG. 7, virtual images of the iris and the crystalline lens are schematically shown by broken lines.

When the control unit 240 obtains the coordinates $(X_v, Y_v, Z_v)$ representing the position of the virtual image by the above process, two-dimensional coordinates $(u_1, v_1)$ when the portion of the three-dimensional coordinates $(X_1, Y_1, Z_1)$ is photographed as the two-dimensional image can be specified. Specifically, at the two-dimensional coordinates $(u_1, v_1)$, a virtual image that appears to be present at the coordinates $(X_v, Y_v, Z_v)$ is captured. Therefore, the control unit 240 acquires the two-dimensional coordinates ($u_1$, $v_1$) corresponding to the three-dimensional coordinates ($X_v$, $Y_v$, $Z_v$) by formulas (6) to (12) based on the correspondence definition data 245*d*. Then, the control unit 240 associates the three-dimensional coordinates ($X_1$, $Y_1$, $Z_1$) with the two-dimensional coordinates ($u_1$, $v_1$).

The control unit 240 executes the above-mentioned process on a plurality of portions of the iris to associate the three-dimensional coordinates (X, Y, Z) with the two-dimensional coordinates (u, v) for the plurality of sites of the iris. Then, the control unit 240 records the information as the correspondence definition data 245*d*, together with the information indicating the target area, in the storage medium 245. The correspondence definition data 245*d* is recorded in association with the two-dimensional image data 245*a* and the three-dimensional image data 245*b* which are data on the images of the eye E to be examined According to the above process, the correspondence definition data 245*d* can be defined, also including the influence of refraction in the cornea.

Figure 6:
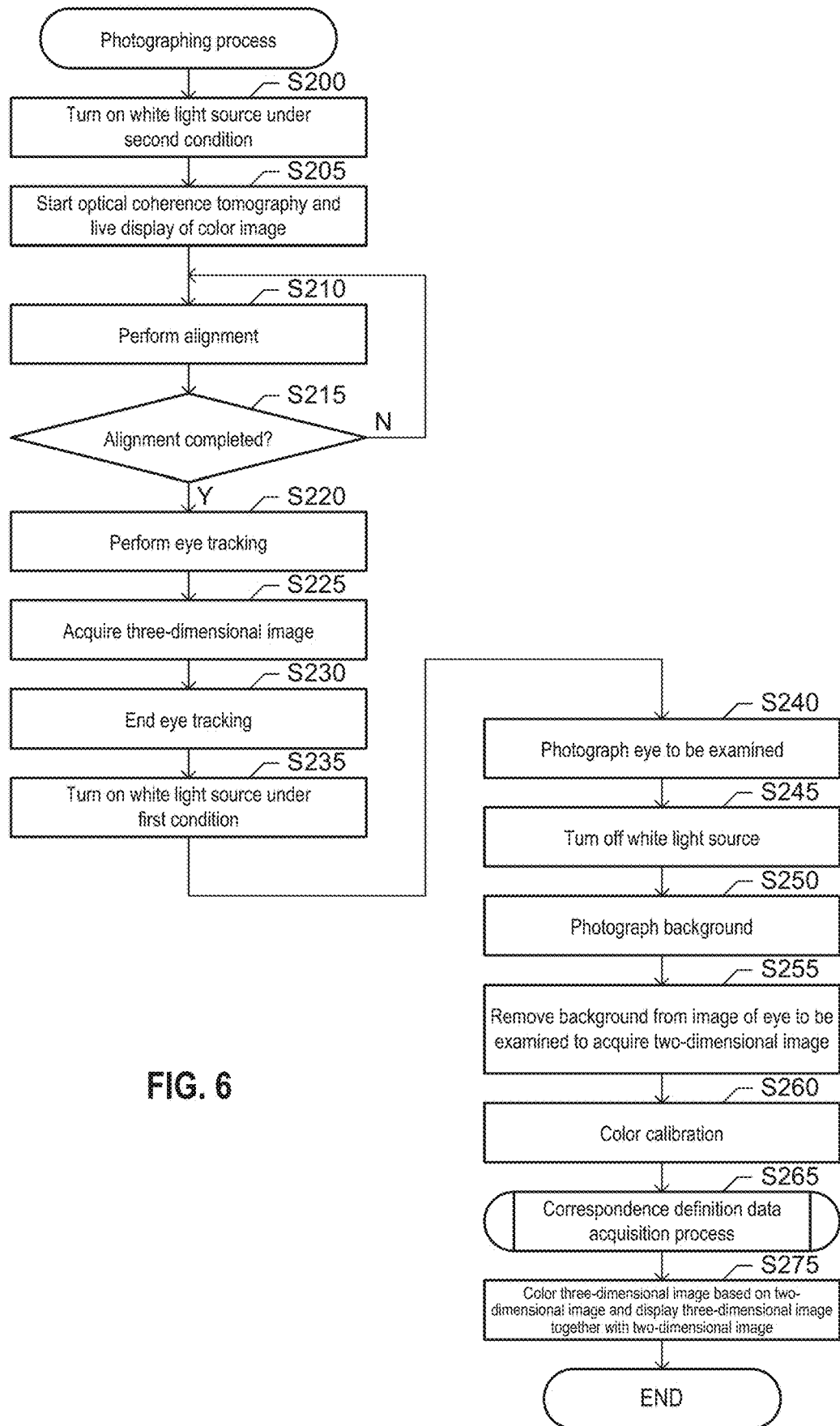
FIG. 6 is a flowchart of photographing process.

When the correspondence definition data 245*d* is recorded in the storage medium 245 in the way as described above, the control unit 240 returns to the photographing process shown in FIG. 6 and continues the process. That is, the control unit 240 colors the three-dimensional image with the two-dimensional image and displays the three-dimensional image together based on the two-dimensional image, using the function of the display control unit 240*d* (step S275). That is, the control unit 240 generates a tomographic image of the section (for example, section designated by the examiner) as the display target based on the three-dimensional image data 245*b* recorded in the storage medium 245.

Then, the control unit 240 determines whether or not the tomographic image contains the three-dimensional coordinates defined by the correspondence definition data 245*d*. When the three-dimensional coordinates defined by the correspondence definition data 245*d* are contained, the control unit 240 specifies the corresponding two-dimensional coordinates based on the correspondence definition data 245*d*, and regards the gradation values in the two-dimensional image as corresponding to the colors of the three-dimensional coordinates. Then, the control unit 240 controls the display 230 to display the tomographic image, and, at the same time, colors the color-specified three-dimensional coordinates based on the gradation values of the corresponding two-dimensional coordinates.

Further, the control unit 240 acquires the two-dimensional image data 245*a* and controls the display 230 to display the two-dimensional image. As a result of the above, for example, the two-dimensional image Ie shown in FIG. 4 and the tomographic images Iov, Ioh and Ior are displayed. Not only the two-dimensional image Ie is color-displayed, but also a predetermined site of the respective tomographic images Iov, Ioh and Ior is color-displayed.

(5) Other Embodiments

The above embodiment is an example for carrying out the present disclosure, and various other embodiments can also be adopted. Therefore, at least a part of the configurations of the above-mentioned embodiment may be omitted or replaced, or at least a part of the processes may be omitted or replaced, or the order thereof may be changed. For example, in the correspondence definition data, steps S300 to S320 may be executed in advance, for example, before shipment. In this case, after the eye E to be examined is photographed, steps S300, S325 and S330 are executed.

Then, the generation of the correspondence definition data 245*d* is completed. Further, the calibration data generation process may be executed at any timing after the shipment of the optical coherence tomographic device 1. Further, the calibration structure is not limited to the structure shown in FIG. 5C. That is, the calibration structure may be a structure having a plurality of reference points such as intersections. Therefore, for example, it may have a shape obtained by cutting a cylinder having an inner wall obliquely with respect to the axis, or may have another three-dimensional structure.

Furthermore, the light sources that are turned on at the time of live display need not be white light sources. For example, light sources that output infrared light or light sources that output green light may be used. Specifically, if the room illumination is bright enough for live display or if the brightness of the fixation target is sufficient for the fixation of the eye to be examined, infrared light illumination can be used, instead of the white light sources, to acquire a live image. Since infrared light reduces glare, the eye E to be examined becomes more stable. Furthermore, in a two-dimensional image captured under infrared light illumination, the texture of the iris is drawn more clearly than in a two-dimensional image captured under white light illumination. Therefore, it can be more easily used as a characteristic point for eye tracking. Further, in a two-dimensional image captured under infrared light illumination, the contrast between the pupil and the iris becomes clearer than in a two-dimensional image captured under white light illumination. Therefore, the position of the center of gravity of the pupil or the like can also be used as a characteristic point for tracking. Furthermore, in a two-dimensional image captured under infrared light illumination, the iris and the contrast between the pupil and the iris can be expressed more clearly than in a two-dimensional image captured under white light illumination.

Furthermore, in a two-dimensional image captured under green light illumination, blood vessels are emphasized more than in a two-dimensional image captured under white light illumination. Therefore, the characteristic point of the blood vessel structure can be easily used as a characteristic point for eye tracking. Further, in a configuration in which a white light source and a light source of another color are provided, each light source may be turned on alternately. The live-displayed two-dimensional image captured under illumination with light of any color may also be used for purposes other than the live display. In this case, the live-displayed two-dimensional image is also stored in the storage medium 245.

The two-dimensional image acquisition unit has only to be able to capture a two-dimensional image by photograph the front surface of the eye E to be examined with the color camera. That is, the color camera has only to be able to photograph the front surface of the eye E to be examined that is the same as the eye E to be examined as the target for optical coherence tomography and to output the image thereof as a color image. The front surface of the eye E to be examined is a front face of the eye E to be examined, and examples of a configuration for photographing the front surface of the eye E to be examined include a configuration in which the eye axis that matches the line-of-sight direction of the eye E to be examined matches the optical axis of the color camera. Of course, since the eye E to be examined moves slightly because of involuntary eye movement during fixation or the like, it is not strictly required that the eye axis matches the optical axis. It suffices that the direction of the eye axis of the eye E to be examined in the fixation state and the optical axis of the color camera substantially match each other, so that the anterior segment of the eye E to be examined can be photographed. Further, since the color camera has only to acquire the two-dimensional image, the color camera has only to be provided with a sensor (area sensor, scannable line sensor, etc.) capable of two-dimensionally photographing visible light reflected from the eye E to be examined. Of course, the number, the form, the arrangement, etc. of the optical elements in the optical system forming the color camera are not limited to the configuration shown in FIG. 2. If an object other than the eye E to be examined (color chart or the like) is arranged in the visual field of the color camera, a two-dimensional image of the object can be acquired under the same conditions as the eye E to be examined (illumination conditions or the like).

The three-dimensional image acquisition unit has only to be able to acquire a three-dimensional image of the eye E to be examined by optical coherence tomography. Optical coherence tomography is a technique involving branching the light from a light source, combining the light reflected by a measurement object and a reference light generation unit (mirror, etc.), and measuring the interference to obtain information on the measurement target in the depth direction of the measurement target (the measurement light traveling direction), and can adopt various methods. Therefore, the method of optical coherence tomography is not limited to the above-mentioned SS-OCT (Swept Source Optical Coherence Tomography), and may be any other method of TD-OCT (Time Domain Optical Coherence Tomography) or Fourier domain, for example, SD-OCT (Spectral Domain Optical Coherence Tomography).

Also, the optical system for performing optical coherence tomography is not limited to the configuration of the above-mentioned embodiment, and the number, form, arrangement, etc. of the optical elements are not limited to the configuration shown in FIG. 1. Of course, the scanning direction of the input light in the galvanometer scanner 202 when acquiring a tomographic image may also be of various modes.

The correspondence definition data generation unit has only to generate correspondence definition data in which the position of a predetermined site of the eye E to be examined in the three-dimensional image when the predetermined site is photographed as a three-dimensional image is associated with the position thereof in the two-dimensional image when the predetermined site is photographed as a two-dimensional image. That is, the correspondence definition data has only to be used to define at which position in the three-dimensional image the same site of the eye E to be examined is photographed and at which position in the two-dimensional image the site is photographed. The predetermined site has only to be a site for which the three-dimensional coordinates of the three-dimensional image are associated with the two-dimensional image of the two-dimensional image, and may be a part of the eye to be examined or the entire eye. Since the two-dimensional image is defined by the gradation values of each pixel, and the colors are defined by the gradation values, the correspondence definition data can define the colors of the three-dimensional image based on the colors of the two-dimensional image. The correspondence definition data has only to define the correspondence between the positions in the respective images, which may be defined in various modes. The present disclosure is not limited to the configuration in which the three-dimensional coordinates of the three-dimensional image are associated with the two-dimensional coordinates of the two-dimensional image, as in the above-mentioned embodiment.

For example, a three-dimensional image obtained by optical coherence tomography shows the structure of the eye E to be examined in a three-dimensional space by superimposing a plurality of tomographic images (two-dimensional images), but the information generated from this information may be used to generate data of another format data and to use the data as the correspondence definition data. More specifically, the three-dimensional image obtained by optical coherence tomography is shown by the gradation value of one channel at each of a plurality of three-dimensional coordinates. Therefore, it is also possible to generate a polygon indicating the surface of the structure of the eye E to be examined (the surface of the eye E to be examined, the iris, etc.) based on the three-dimensional coordinates, to define the position (two-dimensional coordinates, etc.) in the two-dimensional image corresponding to each polygon, and to use the data as correspondence definition data. In this case, the color and texture of each polygon are specified based on the two-dimensional image. Such data may be defined in various modes, but is preferably in a general-purpose format (for example, STL (Stereolithography) data and the like).

Further, the technique of associating the three-dimensional coordinates of the three-dimensional image with the two-dimensional coordinates of the two-dimensional image in the correspondence definition data is not limited to the mode in the above-mentioned embodiment. For example, in the above-mentioned embodiment, the correspondence between arbitrary three-dimensional coordinates and two-dimensional coordinates included in a predetermined site is defined. However, the correspondence between the three-dimensional coordinates and the two-dimensional coordinates at a representative point included in the predetermined site may be defined. In this case, the correspondence between the three-dimensional coordinates and the two-dimensional coordinates at arbitrary coordinates other than the representative point can be calculated by interpolation or the like from the correspondence at a plurality of representative points.

The representative points may be determined by various techniques. For example, the coordinates forming a site having a different characteristic from other sites in the eye E to be examined in the two-dimensional image can represent the representative points. That is, the representative points may be a site where the blood vessels appearing on the surface of the eye E to be examined have a characteristic shape that can be distinguished from the others, and a site where the iris pattern is characteristic and can be distinguished from the others.

When the representative point is a site in a specific color, the process may be performed so as to emphasize the specific color. The process for the emphasis may be any process that emphasizes the intensity of the specific color by comparing it with other colors, and a correction for increasing the intensity of a specific color component of the two-dimensional image or a correction for reducing color components other than the specific color component may be performed, or the color of the illumination may be adjusted. For example, to emphasize red blood vessels, the intensity of the R component may be increased, the intensity of at least one of the G and B components may be reduced, or photographing may be performed under green illumination absorbed by the blood vessels. Furthermore, in order to extract the representative points of the three-dimensional image, an OCT angiography image, which is a three-dimensional non-invasive angiography technique by OCT, may be constructed, and characteristic points such as blood vessel structure may be extracted and used as representative points.

In addition, the representative points may be specified by accepting designation by the examiner, or automatically specified by a characteristic amount extraction algorithm or the like that extracts, for example, a characteristic shape or pattern in a two-dimensional image and a three-dimensional image. When specifying the representative points, a two-dimensional image or a three-dimensional image may be subjected to image processing. For example, information in the depth direction may be added based on the three-dimensional image (additional averaging is also possible), and the representative points may be specified based on an Enface image obtained by projection of the information on a vertical surface in the depth direction.

Various methods can be adopted as a method of specifying the representative points based on the Enface image and associating the three-dimensional coordinates with the two-dimensional coordinates. For example, if homography transformation is used, the Enface image and the two-dimensional image can be associated with each other, and the three-dimensional coordinates and the two-dimensional coordinates can be associated with each other from this correspondence. Specifically, the homography transformation is expressed by the following formula (13).

<IMG SRC="TO19004JPformula-5.bmp"> Mathematical Formula 5

In the formula, $h_{11}$, $h_{12}$, $h_{21}$, and $h_{22}$ are used for rotation including enlargement/reduction of a fixed magnification that is invariant to the coordinate position, and $h_{13}$ and $h_{23}$ are used for translation. $h_{31}$ and $h_{32}$ have a trapezoidal transformation effect in which the scaling magnification changes depending on the coordinate position, and s is a constant coefficient. According to the above formula (13), the coordinates (X, Y) on a plane can be projected onto the coordinates (x, y) on another plane. The parameters such as $h_{11}$ included in the above formula (13) can be determined by specifying the correspondence for a plurality of representative points. Therefore, each parameter can be specified by extracting the number of representative points required for parameter calculation by the examiner's designation or the characteristic amount extraction algorithm, etc., and substituting the representative points into formula (13). As a result of this, the three-dimensional coordinates and the two-dimensional coordinates can be associated with each other. Either of the coordinates (X, Y) and the coordinates (x, y) may be the coordinates of the Enface image or the coordinates of the two-dimensional image.

Furthermore, the representative points may be generated by machine learning or the like. In this case, a machine learning model such as a neural network that inputs a two-dimensional image or a three-dimensional image and outputs the coordinates of representative points is machine-learned. When the machine learning is completed, a two-dimensional image or a three-dimensional image can be input to the machine learning model to specify representative points.

Furthermore, machine learning may be used as a technique for defining the correspondence between the three-dimensional coordinates and the two-dimensional coordinates. Such a configuration can be realized by a configuration that defines a machine learning model which inputs, for example, three-dimensional coordinates and two-dimensional coordinates, and outputs information indicating the correspondence between the three-dimensional coordinates and the two-dimensional coordinates (for example, the coefficients of the conversion formulas in the above-mentioned embodiment). That is, when such machine learning is completed, the three-dimensional coordinates and the two-dimensional coordinates are input to obtain information indicating the correspondence between the two coordinates, and the information can be regarded as correspondence definition data.

The correspondence definition data may be of various modes. For example, in the above-mentioned embodiment, different methods are used to associate the three-dimensional coordinates and the two-dimensional coordinates for the iris portion of the eye E to be examined and for the portions other than the iris. That is, in order to associate the coordinates, the ray tracing is employed for the iris portion, and the internal and external parameters of the color camera are employed for the portions other than the iris. However, the present disclosure is not limited to this mode, and, for example, the coordinates may be associated by ray tracing or using the internal and external parameters of the color camera, for all portions of the eye E to be examined.

The reference color space may be any color space, at least, so long as it suppresses color variation due to the device when the colors of the eye E to be examined are output. Therefore, as described above, in addition to the configuration in which the color space (sRGB, CIEXYZ, CIELAB, etc.) that can express colors without depending on the device is the reference color space, the reference color space may be selected depending on the purpose of using the correspondence definition data. For example, if it is sufficient to ensure that the colors expressed by a specific output device are appropriate colors by using the correspondence definition data, a color space for expressing the colors on the output device may serve as the reference color space. The output device may include various devices such as a display, a printer (including a three-dimensional printer), and a projector.

The color chart is not limited to the standard color chart as long as it has a plurality of color patches that are referred to for color calibration. For example, if the number of color patches close to the colors included in the eye E to be examined is larger than that in the standard color chart, it is possible to increase the possibility that the color calibration of the eye E to be examined is performed more accurately.

It suffices that the white light source generates reflected light in a color equivalent to the color perceived by the examiner and illuminate the eye E to be examined so that the eye E to be examined is photographed with the color, with the color camera. Therefore, the color temperature is not limited to 5500 K in the above-mentioned embodiment, and may be various color temperatures. For example, there may be selected a color temperature that allows the reproduction of a state close to the environment in which the correspondence definition data of the eye E to be examined is used for display or printing.

The calibration data has only to be able to convert the gradation values in the two-dimensional image into gradation values for expressing the colors indicated thereby as the colors of the reference color space. Therefore, the conversion method is not limited to the conversion by the polynomials. For example, a color conversion table indicating the correspondence of the gradation values at the representative points may be defined, and the interpolation calculation may be performed based on the color conversion table, thereby converting the gradation values.

Background removal realized by removing the image captured while turning off the white light sources can be omitted in a situation where there is no background light or a situation where the background light has a small effect. For example, if a two-dimensional image is captured with a light source (for example, a lighting fixture in a room) other than the white light sources included in the ophthalmic device turned off, the background removal may be omitted.

Further, the present disclosure is not limited to the configuration in which, when ray tracing is used, the results of ray tracing and the internal parameter 245*e* and the external parameter 245*f* are used to associate the three-dimensional coordinates with the two-dimensional coordinates. For example, a ray from the eye E to be examined to the area sensor 208 via the lenses (objective lens 204, imaging lens 207) of the color camera may be traced.

Further, the three-dimensional image colored with the color indicated by the two-dimensional image may be variously processed. For example, a three-dimensional image obtained by combining a three-dimensional image of the anterior segment of the eye obtained by optical coherence tomography and a three-dimensional image obtained by OCT angiography may be colored with the colors indicated by the two-dimensional image.

Furthermore, the display mode of the colored three-dimensional image is not limited to the mode as in the above embodiment. For example, a tomographic image in an arbitrary direction obtained from the three-dimensional image may be colored and displayed, or an Enface image (sum in the depth direction) may be colored. Further, a virtual three-dimensional model (a state in which at least a part of the eye E to be examined is expressed in a perspective view) may be colored. Note that, in color display of the three-dimensional image, color configuration based on the calibration data 245*c* may not be executed, and color display may be performed by using the gradation values in the two-dimensional image captured with the color camera. Of course, the three-dimensional image (tomographic image) may be displayed in a state where coloring is not performed, for example, by the examiner's selection. Further, the display using the correspondence definition data is not limited to the colored display. For example, when an arbitrary site of the three-dimensional image is indicated, the site of the corresponding two-dimensional image may be specified based on the correspondence definition data, and the specified site may be shown on the two-dimensional image. Also, when an arbitrary site of the two-dimensional image is designated, the site of the corresponding three-dimensional image may be specified based on the correspondence definition data, and the specified site may be indicated on the three-dimensional image.

What is claimed is:

1. An ophthalmic device comprising:
a two-dimensional image acquisition unit configured to acquire a two-dimensional image by photographing the front of an eye to be examined with a color camera;
a three-dimensional image acquisition unit configured to acquire a three-dimensional image of the eye to be examined by optical coherence tomography; and
a correspondence definition data generation unit configured to generate correspondence definition data in which the position of a predetermined site of the eye to be examined in the three-dimensional image when the predetermined site is photographed as the three-dimensional image is associated with the position of the predetermined site in the two-dimensional image when the predetermined site is photographed as the two-dimensional image.

2. The ophthalmic device according to claim 1, wherein the two-dimensional image acquisition unit is configured to
acquire a chart image that is an image obtained by photographing a color chart having a plurality of color patches with the color camera while illuminating the color chart with a white light source,
acquire calibration data for converting gradation values in the two-dimensional image into gradation values in a reference color space based on gradation values of the plurality of color patches in the chart image and gradation values when colors of the plurality of color patches are expressed in the reference color space,
acquire the two-dimensional image by photographing the eye to be examined with the color camera while illuminating the eye to be examined with the white light source, and
correct the colors of the two-dimensional image based on the calibration data.

3. The ophthalmic device according to claim 2, wherein the calibration data is a coefficient of each term in an n-th order polynomial (wherein n is an integer of 2 or more) for converting the gradation values of the color patches in the chart image into the gradation values in the reference color space.

4. The ophthalmic device according to claim 2, wherein the two-dimensional image acquisition unit is configured to
remove, from the image obtained by photographing the color chart with the color camera while illuminating the color chart with the white light source, an image obtained by photographing the color chart with the color camera while turning off the white light source, thereby acquiring the chart image, and
remove, from the image obtained by photographing the eye to be examined with the color camera while illuminating the eye to be examined with the white light source, an image obtained by photographing the eye to be examined with the color camera while turning off the white light source, thereby correcting the two-dimensional image.

5. The ophthalmic device according to claim 2, wherein an average color rendering index of the white light source is 80 or more.

6. The ophthalmic device according to claim 1, wherein the correspondence definition data is data in which three-dimensional coordinates of the three-dimensional image are associated with two-dimensional coordinates of the two-dimensional image.

7. The ophthalmic device according to claim 6, wherein the correspondence definition data is data for converting the three-dimensional coordinates of the three-dimensional image into the two-dimensional coordinates of the two-dimensional image, based on the relationship between the eye to be examined and the color camera and the characteristics of the optical system of the color camera.

8. The ophthalmic device according to claim 6, wherein the correspondence definition data on the iris of the eye to be examined is data in which the three-dimensional coordinates of the iris are associated with the two-dimensional coordinates thereof, based on ray tracing of rays of light from the iris refracted by the cornea.

9. The ophthalmic device according to claim 3, wherein the two-dimensional image acquisition unit is configured to
remove, from the image obtained by photographing the color chart with the color camera while illuminating the color chart with the white light source, an image obtained by photographing the color chart with the color camera while turning off the white light source, thereby acquiring the chart image, and remove, from the image obtained by photographing the eye to be examined with the color camera while illuminating the eye to be examined with the white light source, an image obtained by photographing the eye to be examined with the color camera while turning off the white light source, thereby correcting the two-dimensional image.

10. The ophthalmic device according to claim 3, wherein an average color rendering index of the white light source is 80 or more.

11. The ophthalmic device according to claim 4, wherein an average color rendering index of the white light source is 80 or more.

12. The ophthalmic device according to claim 9, wherein an average color rendering index of the white light source is 80 or more.

13. The ophthalmic device according to claim 2, wherein the correspondence definition data is data in which three-dimensional coordinates of the three-dimensional image are associated with two-dimensional coordinates of the two-dimensional image.

14. The ophthalmic device according to claim 3, wherein the correspondence definition data is data in which three-dimensional coordinates of the three-dimensional image are associated with two-dimensional coordinates of the two-dimensional image.

15. The ophthalmic device according to claim 4, wherein the correspondence definition data is data in which three-dimensional coordinates of the three-dimensional image are associated with two-dimensional coordinates of the two-dimensional image.

16. The ophthalmic device according to claim 5, wherein the correspondence definition data is data in which three-dimensional coordinates of the three-dimensional image are associated with two-dimensional coordinates of the two-dimensional image.

17. The ophthalmic device according to claim 9, wherein the correspondence definition data is data in which three-dimensional coordinates of the three-dimensional image are associated with two-dimensional coordinates of the two-dimensional image.

18. The ophthalmic device according to claim 10, wherein the correspondence definition data is data in which three-dimensional coordinates of the three-dimensional image are associated with two-dimensional coordinates of the two-dimensional image.

19. The ophthalmic device according to claim 7, wherein the correspondence definition data on the iris of the eye to be examined is data in which the three-dimensional coordinates of the iris are associated with the two-dimensional coordinates thereof, based on ray tracing of rays of light from the iris refracted by the cornea.

20. An ophthalmic device comprising:
a two-dimensional image acquisition unit configured to photograph the front of an eye to be examined with a color camera to acquire a two-dimensional image;
a three-dimensional image acquisition unit configured to acquire a three-dimensional image of the eye to be examined by optical coherence tomography; and
a display control unit configured to display the three-dimensional image colored with colors indicated by the two-dimensional image on a display unit.

* * * * *

UNITED STATES PATENT AND TRADEMARK OFFICE
CERTIFICATE OF CORRECTION

PATENT NO. : 11,642,019 B2
APPLICATION NO. : 16/999937
DATED : May 9, 2023
INVENTOR(S) : Naoko Hara et al.

It is certified that error appears in the above-identified patent and that said Letters Patent is hereby corrected as shown below:

In the Specification

In Column 15, at Line 25, "<IMG SRC="TO19004JPformula-1.bmp"> Mathematical Formula 1" should be changed to:

【Mathematical Formula 1】

$$Rs_n = \alpha_{r0} + \alpha_{r1}R_n + \alpha_{r2}G_n + \alpha_{r3}B_n + \alpha_{r4}R_n^2 + \alpha_{r5}G_n^2 + \alpha_{r6}B_n^2 \\ + \alpha_{r7}R_n^3 + \alpha_{r8}G_n^3 + \alpha_{r9}B_n^3 \cdots (1)$$

$$Gs_n = \alpha_{g0} + \alpha_{g1}R_n + \alpha_{g2}G_n + \alpha_{g3}B_n + \alpha_{g4}R_n^2 + \alpha_{g5}G_n^2 + \alpha_{g6}B_n^2 \\ + \alpha_{g7}R_n^3 + \alpha_{g8}G_n^3 + \alpha_{g9}B_n^3 \cdots (2)$$

$$Bs_n = \alpha_{b0} + \alpha_{b1}R_n + \alpha_{b2}G_n + \alpha_{b3}B_n + \alpha_{b4}R_n^2 + \alpha_{b5}G_n^2 + \alpha_{b6}B_n^2 \\ + \alpha_{b7}R_n^3 + \alpha_{b8}G_n^3 + \alpha_{b9}B_n^3 \cdots (3)$$

Signed and Sealed this
Thirtieth Day of January, 2024

*Katherine Kelly Vidal*

Katherine Kelly Vidal
*Director of the United States Patent and Trademark Office*

In Column 21, at Line 19, "<IMG SRC="TO19004JPformula-2.bmp"> Mathematical Formula 2" should be changed to:

【Mathematical Formula 2】

$$s \begin{bmatrix} u \\ v \\ 1 \end{bmatrix} = \begin{bmatrix} f_x & 0 & c_x \\ 0 & f_y & c_y \\ 0 & 0 & 1 \end{bmatrix} \begin{bmatrix} r_{11} & r_{12} & r_{13} & t_1 \\ r_{21} & r_{22} & r_{23} & t_2 \\ r_{31} & r_{32} & r_{33} & t_1 \end{bmatrix} \begin{bmatrix} X \\ Y \\ Z \\ 1 \end{bmatrix} \quad \cdots (4)$$

In Column 22, at Line 8, "<IMG SRC="TO19004JPformula-3.bmp"> Mathematical Formula 3" should be changed to:

【Mathematical Formula 3】

$$\begin{bmatrix} x \\ y \\ z \end{bmatrix} = R \begin{bmatrix} X \\ Y \\ Z \end{bmatrix} + t \quad \cdots (5)$$

In Column 22, at Line 18, "<IMG SRC="TO19004JPformula-4.bmp"> Mathematical Formula 4" should be changed to:

【Mathematical Formula 4】

$$x' = \frac{x}{z} \quad \cdots (6)$$

$$y' = \frac{y}{z} \quad \cdots (7)$$

$$x'' = x'(1 + k_1 r^2 + k_2 r^4) + 2 p_1 x' y' + p_2 (r^2 + 2 x'^2) \cdots (8)$$

$$y'' = y'(1 + k_1 r^2 + k_2 r^4) + p_1 (r^2 + 2 y'^2) + 2 p_2 x' y' \cdots (9)$$

note that, $r^2 = x'^2 + y'^2 \cdots (10)$ $$u = f_x \cdot x'' + c_x \cdots (11)$$

$$v = f_y \cdot y'' + c_y \cdots (12)$$

In Column 29, at Line 27, "<IMG SRC="TO19004JPformula-5.bmp"> Mathematical Formula 5" should be changed to:

【Mathematical Formula 5】

$$s \begin{bmatrix} X \\ Y \\ 1 \end{bmatrix} = \begin{bmatrix} h_{11} & h_{12} & h_{13} \\ h_{21} & h_{22} & h_{23} \\ h_{31} & h_{32} & 1 \end{bmatrix} \begin{bmatrix} x \\ y \\ 1 \end{bmatrix} \quad \cdots (13)$$